US007939636B2

(12) United States Patent
Moritz et al.

(10) Patent No.: US 7,939,636 B2
(45) Date of Patent: May 10, 2011

(54) REAGENTS FOR THE DETECTION OF PROTEIN PHOSPHORYLATION IN C-SRC SIGNALING PATHWAYS

(75) Inventors: Albrecht Moritz, Salem, MA (US); Kimberly Lee, Seattle, WA (US); John Rush, Beverly, MA (US); Roberto Polakiewicz, Lexington, MA (US)

(73) Assignee: Cell Signaling Technology, Inc., Danver, MA (US)

( * ) Notice: Subject to any disclaimer, the term of this patent is extended or adjusted under 35 U.S.C. 154(b) by 976 days.

(21) Appl. No.: 11/503,335

(22) Filed: Aug. 11, 2006

(65) Prior Publication Data
US 2008/0038752 A1    Feb. 14, 2008

(51) Int. Cl.
*G07K 16/00* (2006.01)
*G07K 16/18* (2006.01)

(52) U.S. Cl. ................................ 530/387.1; 530/387.9

(58) Field of Classification Search ......................... None
See application file for complete search history.

(56) References Cited

U.S. PATENT DOCUMENTS

| | | | |
|---|---|---|---|
| 3,940,475 A | 2/1976 | Gross et al. | |
| 4,289,747 A | 9/1981 | Chu et al. | |
| 4,349,893 A | 9/1982 | Wiegman et al. | |
| 4,376,110 A | 3/1983 | David et al. | |
| 4,474,893 A | 10/1984 | Reading et al. | |
| 4,634,664 A | 1/1987 | Oestberg et al. | |
| 4,634,666 A | 1/1987 | Engleman et al. | |
| 4,659,678 A | 4/1987 | Forrest et al. | |
| 4,676,980 A | 6/1987 | Segal et al. | |
| 4,727,022 A | 2/1988 | Skold et al. | |
| 4,816,397 A | 3/1989 | Boss et al. | |
| 4,816,567 A | 3/1989 | Cabilly et al. | |
| 4,946,778 A | 8/1990 | Ladner et al. | |
| 5,004,692 A | 4/1991 | Tso et al. | |
| 5,092,885 A | 3/1992 | Yamada et al. | |
| 5,112,946 A | 5/1992 | Maione et al. | |
| 5,192,744 A | 3/1993 | Bouck et al. | |
| 5,202,352 A | 4/1993 | Okada et al. | |
| 5,225,539 A | 7/1993 | Winter et al. | |
| 5,260,203 A | 11/1993 | Ladner et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,585,089 A | 12/1996 | Queen et al. | |
| 5,675,063 A | 10/1997 | Knight et al. | |
| 5,677,427 A | 10/1997 | Goldenberg et al. | |
| 5,693,761 A | 12/1997 | Queen et al. | |
| 5,693,762 A | 12/1997 | Queen et al. | |
| 5,789,208 A | 8/1998 | Sharon et al. | |
| 5,969,108 A | 10/1999 | McCafferty et al. | |
| 6,103,889 A | 8/2000 | Whitlow et al. | |
| 6,120,767 A | 9/2000 | Robinson et al. | |
| 6,150,584 A | 11/2000 | Kucherlapati et al. | |
| 6,180,370 B1 | 1/2001 | Queen et al. | |
| 6,329,508 B1 | 12/2001 | Friden et al. | |
| 6,331,415 B1 | 12/2001 | Cabilly et al. | |
| 6,335,163 B1 | 1/2002 | Sharon et al. | |
| 6,355,245 B1 | 3/2002 | Evans et al. | |
| 6,395,718 B1 | 5/2002 | Slusher et al. | |
| 6,407,213 B1 | 6/2002 | Carter et al. | |
| 6,441,140 B1 | 8/2002 | Comb et al. | |
| 6,462,075 B1 | 10/2002 | Bowen et al. | |
| 6,465,431 B1 | 10/2002 | Thorn et al. | |
| 6,475,784 B1 | 11/2002 | Papkoff et al. | |
| 6,482,802 B1 | 11/2002 | Hu et al. | |
| 6,482,810 B1 | 11/2002 | Brem et al. | |
| 6,500,431 B1 | 12/2002 | Gill et al. | |
| 6,500,924 B1 | 12/2002 | Brooks et al. | |
| 6,518,198 B1 | 2/2003 | Klein | |
| 6,521,439 B2 | 2/2003 | Folkman et al. | |
| 6,525,019 B2 | 2/2003 | D'Amato et al. | |
| 6,538,103 B1 | 3/2003 | Ji et al. | |
| 6,544,758 B2 | 4/2003 | O'Reilly et al. | |
| 6,544,947 B2 | 4/2003 | Holaday et al. | |
| 6,548,477 B1 | 4/2003 | Olson et al. | |
| 6,548,640 B1 | 4/2003 | Winter et al. | |
| 6,559,126 B2 | 5/2003 | Tournaire et al. | |
| 6,569,845 B1 | 5/2003 | Futamura et al. | |
| 6,573,256 B2 | 6/2003 | Bishop et al. | |
| 6,783,961 B1 | 8/2004 | Edwards et al. | |
| 6,867,007 B2 | 3/2005 | Kauvar et al. | |
| 6,884,869 B2 | 4/2005 | Senter et al. | |

(Continued)

FOREIGN PATENT DOCUMENTS

EP    0120694    3/1984

(Continued)

OTHER PUBLICATIONS

PharMingen (Transduction Laboratories and PharMingen 1999 Cell Biology Sourcebook, 1999, pp. 242-245).*
Glenney et al (J of Immunological Methods, 1988, 109:277-285).*
Yeatman et al., *Nature Reviews* 4: 470-480 (2004).
Irby et al., *Oncogene* 19: 5636-642 (2000).
Calalb et al., *Mol. Cell. Biol.* 15: 954-963 (1995).
Belsches et al., *Front. Biosci.* 2: d501-518 (1997).
Bache et al., *Eur. J. Biochem* 269: 3881-3887 (1997).

(Continued)

*Primary Examiner* — Laura B Goddard
(74) *Attorney, Agent, or Firm* — Nancy Chiu Wilker

(57) ABSTRACT

The invention discloses 102 novel phosphorylation sites identified in signal transduction proteins and pathways downstream of c-Src kinase, and provides phosphorylation-site specific antibodies and heavy-isotope labeled peptides (AQUA peptides) for the selective detection and quantification of these phosphorylated sites/proteins, as well as methods of using the reagents for such purpose. Among the phosphorylation sites identified are sites occurring in the following protein types: Adaptor/Scaffold proteins, Actin Binding proteins, Cytoskeletal proteins, G protein/GTPase Activating protein/Guanine Nucleotide Exchange Factor proteins, Helicases, RNA Binding proteins, Transcription/Translation Factor or Initiation Complex proteins, Cellular Metabolism Enzymes, and Vesicle proteins.

3 Claims, 8 Drawing Sheets

U.S. PATENT DOCUMENTS

| | | |
|---|---|---|
| 6,979,557 B2 | 12/2005 | Isogai et al. |
| 7,060,268 B2 | 6/2006 | Andya et al. |
| 7,109,000 B2 | 9/2006 | Edinger et al. |
| 7,198,896 B2 | 4/2007 | Rush et al. |
| 7,300,753 B2 | 11/2007 | Rush et al. |

FOREIGN PATENT DOCUMENTS

| | | |
|---|---|---|
| EP | 1184665 | 9/1986 |
| EP | 0239400 | 9/1987 |
| EP | 0404097 | 12/1990 |
| WO | WO 84/03508 | 9/1984 |
| WO | WO 85/03508 | 8/1985 |
| WO | WO 86/01533 | 3/1986 |
| WO | WO 91/10741 | 7/1991 |
| WO | WO 91/17271 | 11/1991 |
| WO | WO 92/01047 | 1/1992 |
| WO | WO 93/11161 | 6/1993 |
| WO | WO 93/12227 | 6/1993 |
| WO | WO 95/20401 | 8/1995 |
| WO | WO 96/27011 | 6/1996 |
| WO | WO 02/00729 | 3/2002 |
| WO | WO 03/016861 | 2/2003 |
| WO | WO 03/089474 | 10/2003 |
| WO | WO 03/106644 | 12/2003 |
| WO | WO 2004/039963 | 12/2003 |
| WO | WO 2004/009618 | 1/2004 |
| WO | WO 2004/066957 | 8/2004 |
| WO | WO 2004/091658 | 10/2004 |
| WO | WO 2005/056825 | 6/2005 |
| WO | WO 2005/083444 | 9/2005 |

OTHER PUBLICATIONS

Schaller et al., *Mol. Cell. Biol.* 14: 1680-1688 (1994).
Shen et al., *Oncogene* 18: 4647-4653 (1999).
U.S. Appl. No. 10/408,486, filed Jul. 4, 2003, Crosby et al.
U.S. Appl. No. 10/781,047, filed Feb. 17, 2004, Gygi et al.
U.S. Appl. No. 10/634,581, filed May 8, 2003, Johnson et al.
U.S. Appl. No. 10/821,234, filed Jul. 4, 2004, LaBat et al.
U.S. Appl. No. 11/077,717, filed Oct. 3, 2005, Lam et al.
U.S. Appl. No. 11/089,368, filed Mar. 25, 2005, Ledbetter et al.
U.S. Appl. No. 11/049,630, filed Feb. 2, 2005, McKinsey et al.
Abu-Duhier et al., "Identification of novel FLT-3 Asp835 mutations in adult acute myeloid leukemia." Br. J. Haematol. 113: 983-988 (2001).
Hardy, et al., "Clinical and Molecular Genetic Analysis of 19 Wolfram Syndrome Kindreds Demonstrating a Wide Spectrum of Mutations in WFS1", Am. J. Hum. Genet. 65:1279-1290 (1999).
Dessein, et al., "Severe Hepatic Fibrosis in Schistoma mansoni Infection is Controlled by a Major Locus That is Closely Linked to the Interferon-y Receptor Gene", Am. J. Hum. Genet. 65:709-721, (1999).
Di Barletta, et al., "Different Mutations in the LMNA Gene Cause Autosomal Dominant and Autosomal Recessive Emery-Dreifuss Muscular Dystrophy", Am. J. Hum. Genet. 66:1407-1412 (2000).
Ebrahimi, et al., "Murine Gammaherpesvirus-68 Infection Causes Multi-Organ Fibrosis and Alters Leukocyte Trafficking in Interferon-y Receptor Knockout Mice", American Journal of Pathology, vol. 158, No. 6 Jun. 2001.
Jemal, et al., "Cancer Statistics 2005", CA: A Cancer Journal for Clinicians, Aug. 26, 2008.
Pollard, et al., "Using Single-Gene Deletions to Identify Checkpoints in the Progression of Systemic Autoimmunity", Annals of the New York Academy of Sciences, Apr. 2003; 987(): 236-9.
Jaskiewicz, et al., "Expression of p53 Tumor Suppressor Gene, Oncoprotein c-erbB-2, Cellular Proliferation and Differentiation n Malignant and Benign Pancreatic Lesions", Anticancer Research 14: 1919-1922 (1994).
Agarwal, et al., "Inositol Hexaphosphate Inhibits Constitutive Activation of NF-xB in Androgen-independent Human Prostate Carcinoma DU145 Cells", Anticancer Research 23:3855-3862 (2003).
Arias-Romero, et al., "A tale of two Paks", Biol. Cell (2008) 100, 97-108.
Bache, et al., "Phosphorylation of Hrs downstream of the epidermal growth factor receptor", Eur. J. Biochem 269, 3881-3881 (2002).
Belsches, et al., "Role of c-Src Tyrosine Kinase in EEGF-Induced Mitogenesis." Frontiers in Bioscience 2,d501-518, Oct. 15, 1997.
G-Amlak, et al., "Reguation of myeloma cell growth through Akt/Gsk3/forkhead signaling pathway", Biochemical and Biophysical Research Sommunications 297 (2002) 760-764.
Radaeva, et al., "Interferon-y inhibits interferon-a signalling in hepatic cells: evidence for the involvement of STAT1 induction and hyperexpression of STAT1 in chronic hepatitis C", Biochem J. (2004) 379, 199-208.
Awasthi, et al., "Novel Function of Human RLIP76: ATP-Dependent Transport of Glutathione Conjugates and Doxorubicin", Biochemistry 2000, 39, 9327-9334.
Jagani, et al., "Foxe tumor suppressors and BCR-ABL-induced leukemia: A matter of evasion of apoptosis", Biochimica et Biophysica Acta 1785 (2008) 63-84.
Hashimoto, et al., "The Breakpoint Cluster Region Gene on Chromosome 22q11 is Associated with Bipolar Disorder", Biol Psychiatry, May 15, 2005;57(10):1097-102.
Bird, et al., "Single-Chain Antigen-Binding Proteins", Science, vol. 242: 423-426, Oct. 21, 1988.
Blood, et al., "Tumor interactions with the vasculature: angiogenesis and tumor metastasis." Biochemica et Biophysica Acta, 1032 (1990) 89-118.
Awasthi, et al., " RLIP76, a non-ABC transporter, and drug resistance in epilepsy", BMC Neuroscience, 2005 6.61.
Boder, et al., "Yeast surface display for screening combinatorial polypeptide libraries" , Nature Biotechnology, vol. 15, 553-557, Jun. 1997.
Bordin, et al., "Band 3 is an anchor protein and a target for SHP-2 tyrosine phosphatase in human erythrocytes", Blood, vol. 100, No. 1, 276-282, Jul. 1, 2002.
Brand, et al., "Fluorescence Probes for Structure1 ", Annu.Rev. Biochem. 1972.41:843-868.
Brennan, et al., "Preparation of Bispecific Antibodies by Chemical Recombination of Monoclonal Immunoglobulin G1 Fragments", Science, vol. 229:81-83, Jul. 5, 1985.
Byers et al., "Rationale for clinical use of immunotoxins in cancer and autoimmune disease" Seminars in Cell Biology 2:59-70 (1991).
Calalb, et al.,"Tyrosine Phosphorylation of Focal Adhesion Kinase at Sites in the Catalytic Domain Regulates Kinase Activity: a Role for Src Family Kinases", Molecular and Cellular Biology, vol. 15, No. 2 Feb. 1995, p. 954-963.
Grand, et al., "p53-Binding Protein 1 is Fused to the Platelet-Derived Growth Factor Receptor B in a Patient with a t(5;15)(q33;q22) and a Imagine-Responsive Eosinophilic Myeloproliferative Disorder", Cancer Research 64, 7216-7219, Oct. 15, 2004.
Carr, et al., "The Need for Guidelines in Publication of Peptide and Protein Identification Data", Molecular & Cellular Proteomics 3.6, 531-533, 2004.
Cell Signaling Technology, "Phospho-PLCgamma1 (Tyr783) Antibody" 2007 Cell Signaling Technology, Inc., Jul. 1-3, 2000.
Accili et al., "FoxOs at the Crossroads of Cellular Metabolism, Differentiation, and Transformation" Cell, vol. 117, 421-426, May 14, 2004, Copyright 2004 by Cell Press.
Chow et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry) 46: 72-78 (2001).
Coia, et al., "Panning and selection of proteins using ribosome display", Journal of Immunological Methods 254 (2001) 191-197.
Crook, et al.,"Repressed by a NuRD", Nature Cel Biology vol. 8 No. 3 Mar. 2006, 212-214.
Cross, et al.,"Serine/Threonine Protein Kinases and Apoptosis", Experimental Cell Research 256, 34-41, 2000.
Czernik, et al.,"Production of Phosphorylation State-Specific Antibodies", Methods in Enzymology, vol. 201, 1991, 264-283.
Daley, et al, "Induction of Chronic Myelogenous Leukemia in Mice by the P210bcr/abl Gene of the Philadelphia Chromosome" Science, vol. 247, 1990, 824-830.
Denslow, et al., "The human Mi-2/NuRD complex and gene regulation", Oncogene (2007) 26, 5433-5438.

Dorahy, et al., "Capture by chemical crosslinkers provides evidence that integrin allbfl3 forms complex with protein tyrosine kinases in intact platelets" Biochem J. (1995) 389, 481-490 (Printed in Great Britain).

Druker, et al., "Imatinib as a Paradigm of Targeted Therapies", Adv. Cancer Res. 2004, 91 (): 1-30.

Edgar, et al., "Flotillin-1: gene structure c DNA cloning from human lung and the identification of alternative polyadenylation signals", The international Journal of Biochemisty & Cell Biology 33 (2001) 53-64.

Blanton, et al., "Schistosomal hepatic fibrosis and the interferon gamma receptor: a linkage analysis using single-nucleotide polymorphic markers", European Journal of Human Genetics (2005) 13, 660-668.

Song, et at., "Lamin A/C mutations associated with familial and sporadic cases of dilated cardiomyopathy in Koreans", Experimental and Molecular Medicine, vol. 39, No. 1, 114-120, Feb. 2007.

Fanger, et al., "Bispecific antibodies and targeted cellular cytotoxicity", Immunol Today, Feb. 1991;12(2):51-4.

Vadlamudi, et al., "Heregulin and HER2 signaling selectively activates c-Src phosphorylation at tyrosine 215" FEBS Letters 543 (2003) 76-80.

Yang, et al "ERK promotes tumorigenesis by inhibiting FOXO3a via MDM2-mediated degradation." Nat Cell Biol. Feb. 2008;10(2):138-48.

Fujita N. et al., "MTA3 and the Mi-2/NuRD complex regulate cell fate during B lymphocyte differentiation." (2004)Cell 119:75-86.

Fujita N. et al., "MTA3; a Mi-2/NuRD Complex Subunit, Regulates an Invasive Growth Pathway in Breast Cancer." (2003) Cell 113:207-19.

Meinhart, et al "A Structural Perspective of CTD Function." Genes Dev. Jun. 15, 2005;19(12):1401-15.

Gerber et al., "Absolute quantification of proteins and phosphoproteins from cell lysates by tandem MS." PNAS, Jun. 2003.

Graves et al. "protein phosphorylation and signal transduction." Pharmacol. Ther. 82: 111-21 (1999).

Griffiths et al. "Human anti-self antibodies with high specificity from phage display libraries." EMBO L., 12:725-734 (1993).

Griffiths et al. "Isolation of high affinity human antibodies directly from large synthetic repertoires." EMBO J. 13:3245-3260 (1994).

Gruber et al. "Efficient tumor cell lysis mediated by a bispecific single chain antibody expressed in *Escherichia coli*." J. Immunol., 152:5368 (1994).

Gu et al. "Phosphotyrosine profiling identifies the KG-1 cell line as a model for the study of FGFR1 fusions in acute myeloid leukemia." Blood First Edition Paper and supplemental table 1, pre-published online Aug. 31, 2006; DOI 10.1182/blood-2006-06-026666, see p. 3 of Table 1, litening under "Hsp70".

Hanes J. et al. "Picomolar affinity antibodies from a fully synthetic naive library selected and evolved by ribosome display." Nat. Biotechnol. 18(12):1287-92(2000).

Heessen S., Fornerod M., "The inner nuclear envelope as a transcription factor resting place." EMBO Rep. 8:914-9 (2007).

Kakumu, et al "Interferon-gamma receptors on T cells in patients with chronic liver disease." Hepatogastroenterology Aug.;35(4):158-61(1988).

Hollinger et al., "Diabodies: small bivalent and bispecific antibody fragments." Proc. Natl. Acaf. Sci. USA, 90:6444-8(1993).

Burwinkel et al "Phosphorylase-kinase-deficient liver glycogenosis with an unusual biochemical phenotype in blood cells associated with a missense mutation in the beta subunit gene (PHKB)." Hum Genet Dec.;101(2):170-4 (1997).

Blume-Jensen et al., "Oncogenic kinase signalling." Nature 411: 355-65 (2001).

Huse w. "Generation of a Large Combinatorial Library of the Immunoglobulin Repertoire in Phage Lambda." Science 246:1275-1281 (1989).

Ingber et al., "Inhibition of Angiogenesis Through Modulation of Collagen Metabolism." Lab. Invest., 59:44-51 (1988).

Htun Van Der Horst, et al "Tyrosine phosphorylation of PYK2 mediates heregulin-induced glioma invasion: novel heregulin/HER3-stimulated signaling pathway in glioma." Int. J Cancer Feb. 20;113(5):689-98 (2005).

Irby et al., "Role of Src expression and activation in human cancer." Oncogene 16: 5636-642 (2000).

Jullien-Flores "Bridging Ral GTPase to Rho pathways" RLIP76, a Ral effector with CDC42/Rac GTPase-activating protein activity. J Cell Chem Sep. 22, 1995;270(38):22473-7.

Hu, et al "HSF-1 interacts with Ral-binding protein 1 in a stress-responsive, multiprotein complex with HSP90 in vivo" J Cell Chem. May 9, 2003;278(19):17299-306.

Birkenkamp, et al "FOXO3a induces differentiation of Bcr-Abl-transformed cells through transcriptional down-regulation of Id1." J Biol. Chem. Jan. 26, 2007;282(4):2211-20.

Goldfinger, et al "RL1P76 (RaIBP1) is an R-Ras effector that mediates adhesion-dependent Rac activation and cell migration." J Cell Biol. Sep. 11, 2006;174(6):877-88.

Dorman, et al "Viral infections in interferon-gamma receptor deficiency." The Journal of Pediatrics Nov.;135(5):640-3(2006).

Kim H. et al., "Epidermal growth factor-dependent association of phosphatidylinositol 3-kinase with the erbB3 gene product" J Biol. Chem., 269(40)24747-24755(1994).

Kohler, et al "Derivation of specific antibody-producing tissue culture and tumor lines by cell fusion." Eur. J. Immunol. 6:511 (1976).

Kostelny et al., "Formation of a Bispecific Antibody by the Use of Leucine Zippers." J. Immunol., 148(5):1547-1557 (1992).

Dorman, et al "Clinical features of dominant and recessive interferon gamma receptor 1 deficiencies." Lancet Dec. 11-17, 2004;364(9451):2113-21.

Merrifield "Solid Phase Peptide Synthesis I, The Synthesis of a Tetrapeptide." J. Am. Chem. Soc. 85:21-49 (1962).

Milstein and Cuello "Hybrid hybridomas and their use in immunohistochemistry." Nature, 305:537-540(1983).

Radziwill, et al "The Bcr kinase downregulates Ras signaling by phosphorylating AF-6 and binding to its PDZ domain." Mol. Cell Biol. Jul. 2003;23(13):4663-42.

Morrison et al., "Chimeric human antibody molecules: Mouse antigen-binding domains with human constant region domains." Proc. Nat'l Acad. Sci. 81: 6851(1984).

Moses et al., "Identification of an Inhibitor of Neovascularization from cartilage." Science, 248:1408-1410 (1990).

Mullinax et al., "Identification of human antibody fragment clones specific for tetanus toxoid in a bacteriophage gamma immunoexpression library." Proc. Nat'l Acad. Sci. 87: 8095(1990).

Nakamura, Y., "Codon usage tabulated from international DNA sequence databases: status for the year 2000." Nucleic Acids Res. Jan. 1;28:292 (2000).

Nardi, et al., "Mechanisms and implications of imatinib resistance mutations in BCR-ABL." Curr. Opin. Hematol. 11:35-43(2003).

Shackleton, et al "LMNA, encoding lamin A/C, is mutated in partial lipodystrophy." Nat. Genet. Feb. 2000;24(2):153-6.

Shankaran, et al "IFN gamma and lymphocytes prevent primary tumour development and shape tumour immunogenicity." Nature Apr. 26, 2001; 410(6832): 1107-11.

Feske, et al "A mutation in Orai1 causes immune deficiency by abrogating CRAC channel function." Nature May 11, 2006;441 (7090):179-85.

Neuberger, et al "Recombinant antibodies possessing novel effector functions." Nature. Dec. 1984 13-9, ; 312(5995):604-8.

Newman et al., "Primatization of Recombinant Antibodies for Immunotherapy of human Diseases: A Macaque/Human Chimeric Antibody Against Human CD4." BioTechnology, 10: 1455-1460(1992).

Nissim et al., "Antibody fragments from a 'single pot' phage display library as immunochemical reagents." EMBO J. Feb. 1, 1994;13(3):692-8.

Ostberg, et al.,"Human x (Mouse x Human) Hybridomas Stably Producing Human Antibodies", Hybridoma, vol. 2, No. 4, 1983, 361-367.

Olayioye, et al.," The ErbB signaling network: receptor heterodimerization in development and cancer", The EMBO Journal vol. 19 No. 13 pp. 3159-3167, 2000.

Liu, et al., "Induction of prosurvival molecules by apoptotic stimuli: involvement of FOX03a and ROS", Oncogene (2005) 24, 2020-2031.

Order, et al., "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985).

Paweletz, et al., "Reverse phase protein microarrays which capture disease progression show activation of pro-survival pathways at the cancer invasion front", Oncogene (2001) 20, 1981-1989.

Pluckthun et al., "Antibodies from *Escherichia coli*" The Pharmacology of Monoclonal Antibodies, vol. 113, Rosenburg and Moore, eds. (Springer-Verlag New York, 1994), pp. 269-315.

Prigent, et al., "Identification of c-erbB-3 binding sites for phosphatidylinositol 3'-kinase and SHC using an EGF receptor/c-erbB-3 chimera" The EMBO Journal vol. 13 No. 12 pp. 2831-2841, 1994.

Cao, Kan "A lamin a protein isoform over expressed in Hutchinson-Gilford progeria syndrome interferes with mitosis in progeria and normal cells" Proc. Natl. Acad. Sci U S A. Mar. 20, 2007;104(12):4949-54.

Dechat, H. "Alterations in mitosis and cell cycle progression caused by a mutant lamin a known to accelerate human aging." Proc. Natl. Acad. Sci U S A. Mar. 20, 2007;104(12):4955-60.

Hanes, J. "In vitro selection and evolution of functional proteins by using ribosome display" Proc. Natl. Acad. Sci. U. S. A. 94(10):4937-42 (1997).

Hanes, J. "Ribosome display efficiently selects and evolves high-affinity antibodies in vitro from immune libraries." Proc. Natl. Acad. Sci. U. S. A. 95(24):14130-5 (1998).

Masui, et al., "A possible association between missense polymorphism of the breakpoint cluser region gene and lithium prophylaxis in bipolar disorder", Progress in Neuro-Psychopharmacogy & Biological Psychiatry 32 ( 2008) 204-208.

Reddy, et al., "Transcriptional repression mediated by repositioning of genes to the nuclear lamina" Vole 452 Mar. 13, 2008 doi:10.1038/Nature 06727.

Rosnet, et al.,"Hematopoietic Receptors of Class III Receptor-type Tyrosine Kinases", Critical Reviews in Ontogenesis, 4 (6): 595-613 (1993).

Rush, et al., " Immunoaffinity Profiling of Tyrosine Phosphorylation in Cancer Cells," Nature Biotechnology, 23(1): 94-101 (2005).

Schaller, et al.,"Autophosphorylation of the Focal Adhesion Kinase, pp125FAK Directs SH2- Dependent Binding of pp60src", Molecular and Cellular Biology, Mar. 1994, p. 1680-1688.

Schindler, et al., "Structural Mechanism for STI-571 Inhibition of Abelson Tyrosine Kinase", Science 289: 1938-1942 (2000).

Schreiber, et al., "Target-Oriented and Diversity-Oriented Organic Synthesis in Drug Discovery", Science 287, 1964-1969 (2000).

Castrillon, et al., "Suppression of Ovarian Follicle Activation in Mice by the Transcription Factor Foxo3a", Science 301, 215-218 2003.

Shalaby, et al., "Development of Humanized Bispecitic Antibodies Reactive with Cytotoxic Lymphocytes and Tumor Cells Overexpressing the HER2 Protooncogene", J. Exp. Med. vol. 175 Jan. 1992 217-225.

Shen, et al.,"Evidence for SH3 domain directed binding and phosphorylation of Sam68 by Src", Oncogene 18 4647-4653 (1999).

Spira, et al.,"The identification of monoclonal class switch variants by Sib Selection and an Elisa Assay", Journal of Immunological Methods, 74 (1984) 307-315.

Steplewski, et al., "Isolation and characterization of anti-monosialoganglioside monoclonal antibody 19-9 class-switch variants ", Proc. Nat'l. Acad. Sci., USA vol. 82 pp. 8653-8657, Dec. 1985.

Stryer, et al., "Fluorescence Spectroscopy of Proteins" Science, vol. 162 1968 526-533.

Suresh, et al., "Bispecific monoclonal antibodies from hybrid hybridomas" Methods in Enzymology, vol. 121 1986 210-228.

Tutt, et al., "Trispecific F(ab'), Derivatives That Use Cooperative Signaling Via the TCR/CD3 Complex and CD2 to Activate and Redirect Resting Cytotoxic T Cells" The Journal of Immunology 147(1):60-9 (1991).

Upstate, et al., "Antibodies for Phosphorylation & Beyond", Internet Article, Jun. 2004, 1-16.

Vadlamudi, et al., "Heregulin and HER2 signaling selectively activates c-Src phosphorylation at tyrosine 215" Febs Letters 543. 2003, 76-80.

Vijapurkar, et al.,"Roles of mitogen- activated protein kinase and phosphoinositide 3'kinase in ErbB2/ErbB3 coreceptor-mediated heregulin signaling" Experimental Cell Research 284, 2003, 291-302.

Walker. et al., "Interaction of Human IgG Chimeric Antibodies With the Human FcRII Receptors: Requirements for Antibody-Mediated Host Cell-Target Cell Interaction" Molecular Immunology, vol. 26 No. 4, pp. 403-411 1989.

Wetzel, et al., Evaluation of CML model cell lines ad imatinib mesylate response: Determinants of signaling profiles. Journal of Immunological Methods, 2005.

Yamamoto, et al., "Activating mutation of D835 within the activation loop of FLT3 in human hematologic malignancies" Blood, Apr. 15, 2001 vol. 97, No. 8 2434-2439.

Yang, et al., "Lysine acetylation and the bromodomian: a new partnership for signaling", BioEssays, 2004, vol. 26, Iss 10, 1076-1087.

Yeatman, et at, "A Renaissance for SRC", Nature Reviews 4: 2004, 470-480.

Yeung, et al., "Quantitative Screening of Yeast Surface-Displayed Polypeptide Libraries by Magnetic Bead Capture" Biotechnol. Prog. 2002, 18(2):212-20.

Yokota, et al., "Internal tandem duplication of the FLT3 gene is preferentially seen in acute myeloid leukemia and myelodysplastic syndrome among various hematological malignancies. A study on a large series of patients and cell lines", Leukemia 1997 11: 1605-1609.

Zapata, et al., "Engineering linear F (ab')2 fragments for efficient production in *Escherichia coli* and enhanced antiproliferative activity" Protein Engineering vol. 8 No. 10 pp. 1057-1062, 1995.

Zhang, et al., "Phosphoprotein Analysis Using Antibodies Broadly Reactive against Phosphorylated Motifs" Journal of Biological Chemistry, 2002, vol. 227, pp. 39379-39387.

Laird, et al., "Src Family Kinase Activity is Required for Signal Tranducer and Activator of Transcription 3 and Focal Adhesion Kinase Phosphorylation and Vascular Endothelial Growth Factor Signaling in Vivo and for Anchorage-dependent and independent Growth of Human Tumor Cells," Molecular Cancer Therapeutics, vol. 2, 461-467, May 2003.

Webb, et al., "FAL-Src signaling through paxillin, ERK and MLCK regulates adhesion disability" Nature Cell Biology, vol. 6, No. 2, 154-161, Feb. 2004.

Calalb, et al., "Tyrosine Phosphorylation of Focal Adhesion Kinase at Sites in the Catalytic Domain Regulates Kinase Activity: a Role for Src Family Kinases," Molecular and Cellular Biology, vol. 15 No. 2, 954-962, Feb. 1995.

Vitelli, et al., "Molecular Cloning and Expression Analysis of the Human Rab7 GTP-ase Complimentary Deoxyribonucleic Acid," Biochemical and Biophysical Research Communications, 229, 887-890 (1996).

Basrur, et al., Proteomic Analysis of Early Melanosomes: Identification of Novel Melanosomal Proteins, Journal of Proteome Research, 2, 69-79 (2003).

Oegema, et. al., "Functional Analysis of a Human Homologue of *Drosophila* Actin Binding Protein Anillin Suggests a Role in Cytokinesis," The Journal of Cell Biology, vol. 150, No. 3, 539-551 Aug. 2000.

\* cited by examiner

FIGURE 2

| Protein Name (short) | Protein Name (full) | Accession Number | Protein Type | Phospho-Residue | Phosphorylation Site Sequence | SEQ ID NO: |
|---|---|---|---|---|---|---|
| anillin | anillin | Q8K298 | Actin binding protein | Y666 | SEDRDLLySIDAYRS | SEQ ID NO: 1 |
| catenin, delta-1 | catenin src | P30999 | Actin binding protein | Y217 | PDGYGRHyEDGYPGG | SEQ ID NO: 2 |
| catenin, delta-1 | catenin src | P30999 | Actin binding protein | Y221 | GRHYEDGyPCGSDNY | SEQ ID NO: 3 |
| catenin, delta-1 | catenin src | P30999 | Actin binding protein | Y257 | APSRQDVyGPQPQVR | SEQ ID NO: 4 |
| catenin, delta-1 | catenin src | P30999 | Actin binding protein | Y280 | HRFHPEPyGLEDDQR | SEQ ID NO: 5 |
| catenin, delta-1 | catenin src | P30999 | Actin binding protein | Y334 | EEVPPDQyYWAPLAQ | SEQ ID NO: 6 |
| catenin, delta-1 | catenin src | P30999 | Actin binding protein | Y96 | QDHNHLLySTIPRMQ | SEQ ID NO: 7 |
| Filamin B | exp. seq. AL024016 | Q80X90 | Actin binding protein | Y2502 | RSSTETCySAIPKSS | SEQ ID NO: 8 |
| IRSp53 | angiogenesis inhib. assoc. 2 | Q91V97 | Actin binding protein | Y338 | QSKLSDSySNTLPVR | SEQ ID NO: 9 |
| IRSp53 | angiogenesis inhib. assoc. 2 | Q91V97 | Actin binding protein | Y492 | GTFKQRPySVAVPAF | SEQ ID NO: 10 |
| IRSp53 | angiogenesis inhib. assoc. 2 | Q91V97 | Actin binding protein | Y506 | FSQGLDDyGARSVSR | SEQ ID NO: 11 |
| tensin 2 | tensin 2 | Q8C)95 | Actin binding protein | Y460 | GPLDGSPyAQVQRVP | SEQ ID NO: 12 |
| Cbl-b | Cbl-b | P70451 | Adaptor/scaffold | Y1014 | ASQDyDQLPSSSD | SEQ ID NO: 13 |
| CrkL | Crk | P47941 | Adaptor/scaffold | Y251 | QKRVPCAyDKTALAL | SEQ ID NO: 14 |
| DAB2 | disabled homolog 2 | P98078 | Adaptor/scaffold | Y342 | PLNVDTDyFGQQFDQ | SEQ ID NO: 15 |
| Dok1 | DOK1 | P97465 | Adaptor/scaffold | Y336 | VHSKKPLyWDLYGHV | SEQ ID NO: 16 |
| Dok1 | DOK1 | P97465 | Adaptor/scaffold | Y340 | KPLYWDLyGHVQQQL | SEQ ID NO: 17 |
| Dok1 | DOK1 | P97465 | Adaptor/scaffold | Y401 | EEGYELPyNPATDDY | SEQ ID NO: 18 |
| Eps8 | EGFR substrate 8 | Q08509 | Adaptor/scaffold | Y490 | DYPPADGyAYSSSMY | SEQ ID NO: 19 |
| Eps8 | EGFR substrate 8 | Q08509 | Adaptor/scaffold | Y492 | PPADGYAySSSMYHR | SEQ ID NO: 20 |
| LIM | enigma homolog 1 | Q9QYN2 | Adaptor/scaffold | Y251 | VERNTEFyHIPTHSD | SEQ ID NO: 21 |
| P130Cas | p130 Cas | Q61140 | Adaptor/scaffold | Y228 | RVGQQYVvEAAQTEQ | SEQ ID NO: 22 |
| P130Cas | p130 Cas | Q61140 | Adaptor/scaffold | Y366 | SPAAEDVyDVPPPAP | SEQ ID NO: 23 |
| P130Cas | p130 Cas | Q61140 | Adaptor/scaffold | Y376 | PPPAPDLyDVPPGLR | SEQ ID NO: 24 |
| RA70 | Src-assoc. adaptor protein | Q922K4 | Adaptor/scaffold | Y197 | CAPDKRIyQFTAASP | SEQ ID NO: 25 |
| RA70 | Src-assoc. adaptor protein | Q922K4 | Adaptor/scaffold | Y260 | QPIDDEIyEELPEEE | SEQ ID NO: 26 |
| RA70 | Src-assoc. adaptor protein | Q922K4 | Adaptor/scaffold | Y75 | DAEDGDEyDDPFAGP | SEQ ID NO: 27 |
| Shb | similar to SHB adapt. pro. B | XP_131399 | Adaptor/scaffold | Y113 | RAMCRLDyCGGGGGG | SEQ ID NO: 28 |
| tensin 1 | tensin | Q7TPM8 | Adaptor/scaffold | Y213 | SLDRHAAyGGYSTPE | SEQ ID NO: 29 |
| tensin 1 | tensin | Q7TPM8 | Adaptor/scaffold | Y216 | RHAAYGGySTPEDRR | SEQ ID NO: 30 |
| ZO1 | tight junction protein 1 | P39447 | Adaptor/scaffold | Y1164 | EEQPAPAyEVHNRYR | SEQ ID NO: 31 |
| ZO1 | tight junction protein 1 | P39447 | Adaptor/scaffold | Y1177 | YRPEAQPySSTGPKS | SEQ ID NO: 32 |
| ZO2 | tight junction protein 2 | Q9Z0U1 | Adaptor/scaffold | Y554 | VREDAVLyLLEIPKG | SEQ ID NO: 33 |
| LPP | Lipoma-preferred-partner | Q8BFW7 | Adaptor/scaffold; Cytoskeletal protein | Y245 | GPSSGQIyGPGPRGY | SEQ ID NO: 34 |
| LPP | Lipoma-preferred-partner | Q8BFW7 | Adaptor/scaffold; Cytoskeletal protein | Y301 | QGRYYEPyYAAGPSY | SEQ ID NO: 35 |
| EPS15R | EGFR substrate 15 | Q60902 | Adaptor/scaffold; Vesicle protein | Y562 | AHRSLEQyDQVPDGV | SEQ ID NO: 36 |
| protocadherin 7 | protocadherin 7 | O88185 | Adhesion | Y948 | KKSKQPLySIVTVE | SEQ ID NO: 37 |
| SREC-II | scavenger receptor class F | P59222 | Adhesion | Y615 | EGPSGALyARVARRE | SEQ ID NO: 38 |
| annexin A2 | similar to Annexin II | P07356 | Calcium-binding protein | Y23 | HSTPPSAyGSVKPYT | SEQ ID NO: 39 |
| annexin A2 | annexin A2 | P07356 | Calcium-binding protein | Y237 | RYKSYSPyDMLESIK | SEQ ID NO: 40 |
| NEDD5 | septin 2 | P42208 | Cell cycle regulation | Y17 | INPETPGyVGFANLP | SEQ ID NO: 41 |
| septin 7 | cdc10 homolog | O55131 | Cell cycle regulation | Y318 | RKLAAVTyNGVDNNK | SEQ ID NO: 42 |
| CD34 antigen | CD34 antigen | Q64314 | Cell surface | Y326 | ERLGEDPyYTENGGG | SEQ ID NO: 43 |
| CD34 | CD34 antigen | Q64314 | Cell surface | Y336 | ENGGGQGySSGPGAS | SEQ ID NO: 44 |
| HSC70 | heat shock protein 8 | P08109 | Chaperone | Y15 | GIDLGTTySCVGVFQ | SEQ ID NO: 45 |
| actin, beta | actin, beta, cytoplasmic | P70514 | Cytoskeletal protein | Y166 | VTHTVPIyEGYALPH | SEQ ID NO: 46 |
| actin, gamma, similar to | similar to actin gamma | XP_134663 | Cytoskeletal protein | Y53 | GMGQKDSyVGDKAQS | SEQ ID NO: 47 |
| actinin, alpha 4 | actinin alpha 4 | P57780 | Cytoskeletal protein | Y266 | MTYVSSFyHAFSGAQ | SEQ ID NO: 48 |
| DAL-1 | DAL1P | Q9WV92 | Cytoskeletal protein | Y479 | AEVGTGQyATTKGIS | SEQ ID NO: 49 |
| ELMO2 | engulfment and cell mot. 2 | Q8BHL5 | Cytoskeletal protein | Y48 | WSLPNPEyYTLRYAD | SEQ ID NO: 50 |
| EPB41L2 | erythr. pro. band 4.1 like 2 | O70318 | Cytoskeletal protein | Y606 | RVDGDNIyVRHSNLM | SEQ ID NO: 51 |

FIGURE 2 (continued)

| | A | B | C | D | F | G | H |
|---|---|---|---|---|---|---|---|
| 53 | EPB41L2 | erythr. pro. band 4.1 like 2 | O70318 | Cytoskeletal protein | Y889 | TETKTTIyESPQIDG | SEQ ID NO: 52 |
| 54 | eplin | epithel. pro. lost in neoplasm | Q9ERG0 | Cytoskeletal protein | Y746 | QIKRNRYyDEDEDEE | SEQ ID NO: 53 |
| 55 | plectin 1 | exp. sequ. AA591047 | XP_128277.4 | Cytoskeletal protein | Y3579 | SKGYYSPySVSGSGS | SEQ ID NO: 54 |
| 56 | talin 1 | talin | P26039 | Cytoskeletal protein | Y1116 | IAQGNENyAGIAARD | SEQ ID NO: 55 |
| 57 | vimentin | vimentin | P20152 | Cytoskeletal protein | Y52 | PSTSRSLySSSPGGA | SEQ ID NO: 56 |
| 58 | vimentin | vimentin | P20152 | Cytoskeletal protein | Y60 | SSSPGGAyVTRSSAV | SEQ ID NO: 57 |
| 59 | cortactin | cortactin | Q60598 | Cytoskeletal protein; Actin binding protein | Y215 | KSAVGFEyQGKTEKH | SEQ ID NO: 58 |
| 60 | enolase, alpha | enolase 1 | P17182 | Enzyme, cellular metabolism | Y24 | PTVEVDLyTAKGLFR | SEQ ID NO: 59 |
| 61 | G6PD-2 | G6PDH 2 | P97324 | Enzyme, cellular metabolism | Y506 | GFQYKGTyKGTHKH | SEQ ID NO: 60 |
| 62 | GAPDH | GAPDH | P16858 | Enzyme, cellular metabolism | Y315 | ISWYDNEyGYSNRVV | SEQ ID NO: 61 |
| 63 | phosphoglycerate mutase 1 | phosphoglycerate mutase 1 | Q9DBJ1 | Enzyme, cellular metabolism | Y25 | ENRFSGWyDACLSPA | SEQ ID NO: 62 |
| 64 | similar to GAPDH | sim. to GAPDH | XP_195632 | Enzyme, cellular metabolism | Y154 | ISWYNNEyGYSNREE | SEQ ID NO: 63 |
| 65 | Rab7 | RAB7 | P51150 | G protein, Rab | Y183 | QETEVELyNEFPEPI | SEQ ID NO: 64 |
| 66 | centaurin-beta 2 | RIKEN cDNA 9530039915 | XP_193836.3 | GTPase activating protein, ARF | Y773 | MRESEGLyGQPGDET | SEQ ID NO: 65 |
| 67 | GIT1 | similar to GIT1 | XP_126291.5 | GTPase activating protein, ARF | Y562 | ELEDDAIySVHVPAG | SEQ ID NO: 66 |
| 68 | GIT1 | similar to GIT1 | XP_126291.5 | GTPase activating protein, ARF | Y571 | VHVPAGLyRIRKGVS | SEQ ID NO: 67 |
| 69 | IQGAP1 | Cdc42-Rac1 effector | Q9JKF1 | GTPase activating protein, Ras | Y1510 | LVKLQQTySALNSKA | SEQ ID NO: 68 |
| 70 | IQGAP1 | Cdc42-Rac1 effector | Q9JKF1 | GTPase activating protein, Ras | Y172 | APQIQDLyGKVDFTE | SEQ ID NO: 69 |
| 71 | RasGAP 3 | RAS p21 protein activator 3 | Q60790 | GTPase activating protein, Ras | Y765 | DGPEQEEySTFVIDD | SEQ ID NO: 70 |
| 72 | Rin1 | Ras and Rab Interactor 1 | Q92IQ7 | Guanine nucleotide exchange factor, Rab | Y35 | KPSTDPLyDTPDTRG | SEQ ID NO: 71 |
| 73 | Tiam1 | T-cell lymph. inv. and met. 1 | Q60610 | Guanine nucleotide exchange factor, Rac/Rho | Y1323 | GSHRLSIyEEWDPFR | SEQ ID NO: 72 |
| 74 | DDX3 | DEAD box polypeptide 3 | Q62167 | Helicase | Y103 | DDRGRGDyDGIGGRG | SEQ ID NO: 73 |
| 75 | DBY | DEAD box polypeptide 3 | Q9QWS9 | Helicase; RNA binding protein | Y104 | DDHGRNDyDGIGGRD | SEQ ID NO: 74 |
| 76 | PL10 | PL10 protein | P16381 | Helicase; RNA binding protein | Y67 | WSKDKDAySSFGSRS | SEQ ID NO: 75 |
| 77 | TAGE4 | hypothet. pro. D7Ertd458e | Q60977 | Immunoglobulin superfamily | Y398 | SERENVQySSVNGDC | SEQ ID NO: 76 |
| 78 | PI3K p85-beta | PI3K p85 beta subunit | O08908 | Kinase, lipid | Y458 | SREYDQLyEEYTRTS | SEQ ID NO: 77 |
| 79 | glutamyl-prolyl-tRNA synthetase | glutamyl-prolyl-tRNA synth. | Q8CGC7 | Ligase | Y690 | PYEPVSPySCREAPC | SEQ ID NO: 78 |
| 80 | MRCK-beta | Cdc42 BP kinase beta | Q7TT50 | Protein kinase, Ser/Thr (non-receptor) | Y954 | FQDSIFEyFNTAPLA | SEQ ID NO: 79 |
| 81 | MYPT1 | PP1 reg. subunit 12A | Q9DBR7 | Protein phosphatase, dual-specificity | Y764 | SRTYDETyTRYRPVS | SEQ ID NO: 80 |
| 82 | RAIG1 | retinoic acid induc. pro. 3 | Q8BHL4 | Receptor, GPCR | Y346 | AQAPASPyNDYEGRK | SEQ ID NO: 81 |
| 83 | RAIG1 | retinoic acid induc. pro. 3 | Q8BHL4 | Receptor, GPCR | Y349 | PASPYNDyEGRKGDS | SEQ ID NO: 82 |
| 84 | PTP-delta | PTP, receptor type delta, B | Q64487 | Receptor, protein phosphatase, tyrosine | Y666 | NSSDTTKyLLEQLEK | SEQ ID NO: 83 |
| 85 | PTP-delta | PTP, receptor type delta, B | Q64487 | Receptor, protein phosphatase, tyrosine | Y677 | QLEKWTEyRITVTAH | SEQ ID NO: 84 |
| 86 | RPL3 | ribosomal protein L3 | P27659 | Ribosomal protein | Y306 | KNNASTDyDLSDKSI | SEQ ID NO: 85 |
| 87 | FXR1 | fragile X mental retard. gene 1 | Q61584 | RNA binding protein | Y506 | KDPDSNPySLLDNTE | SEQ ID NO: 86 |
| 88 | FXR2 | similar to fragile X | Q9WVR4 | RNA binding protein | Y520 | KDPDSNPySLLDTSE | SEQ ID NO: 87 |
| 89 | RBM3 | RNA binding motif protein 3 | O89086 | RNA binding protein | Y139 | YSGSQGGyDRYSGGN | SEQ ID NO: 88 |
| 90 | ZNF289 | zinc finger protein 289 | Q9D758 | Transcription factor | Y458 | GREVDSEyEARSRLQ | SEQ ID NO: 89 |
| 91 | eIF3E | eIF3 subunit 6 | P60229 | Translation initiation complex | Y445 | ATQDSGFy | SEQ ID NO: 90 |
| 92 | PTRF | Pol 1 release factor | O54724 | Translation initiation complex | Y310 | FTPDHVVyARSKTAV | SEQ ID NO: 91 |
| 93 | eEF1A-1 | elongation factor 1 alpha 1 | P10126 | Translation initiation complex | Y29 | TTTGHLIyKCGGIDK | SEQ ID NO: 92 |
| 94 | eIF4H | Williams-Beuren syndrome | Q9WUK2 | Translation initiation complex | Y12 | DTYDDRAySSFGGGR | SEQ ID NO: 93 |
| 95 | eIF4H | Williams-Beuren syndrome | Q9WUK2 | Translation initiation complex | Y45 | TEPPYTAyVGNLPFN | SEQ ID NO: 94 |
| 96 | mahogunin | mahogunin | Q9D074 | Ubiquitin conjugating system | Y389 | AIPSAPLyEEITYSG | SEQ ID NO: 95 |
| 97 | mahogunin | mahogunin | Q9D074 | Ubiquitin conjugating system | Y394 | PLYEEITySGISDGL | SEQ ID NO: 96 |
| 98 | Clathrin heavy chain 1 | RIKEN cDNA 3110065L21 | Q80U89 | Vesicle protein | Y910 | FLRENPYyDSRVVGK | SEQ ID NO: 97 |
| 99 | Munc-18a | syntaxin binding protein 1 | O08599 | Vesicle protein | Y473 | ERISEQTyQLSRWTP | SEQ ID NO: 98 |
| 100 | SH3 domain protein 2B | SH3 domain protein 2B | Q62419 | Vesicle protein | Y315 | QPSCKALyDFEPEND | SEQ ID NO: 99 |
| 101 | sorting nexin 9 | sorting nexin 9 | Q91VH2 | Vesicle protein | Y239 | IAIIVGDyGPMWVYP | SEQ ID NO: 100 |
| 102 | EHD1 | EH-domain containing 1 | Q9WVK4 | Vesicle protein; Calcium-binding protein | Y453 | PTYDEIFyTLSPVNG | SEQ ID NO: 101 |
| 103 | dynamin-1 | dynamin | P39053 | Vesicle protein | Y354 | SGDQIDTyELSGGAR | SEQ ID NO: 102 |

| Seq | # | b | y | (+1) |
|---|---|---|---|---|
| R | 1 | 157.2 | — | 8 |
| V | 2 | 256.3 | 1089.1 | 7 |
| P | 3 | 353.4 | 933.0 | 6 |
| C | 4 | 513.6 | 833.8 | 5 |
| A | 5 | 584.7 | 736.7 | 4 |
| *Y | 6 | 827.9 | 576.5 | 3 |
| D | 7 | 943.0 | 505.5 | 2 |
| K | 8 | 1071.1 | 262.3 | 1 |
|   |   |   | 147.2 |   |

RVPCApYDK

EKPSTDPLpYDTPDTR

| Seq # | b | y | (+1) | Seq | # | b | y | (+2) |
|---|---|---|---|---|---|---|---|---|
| | | | | | | | | |
| E 1 | 130.1 | 1815.8 | 15 | E | 1 | 65.6 | 908.4 | 15 |
| K 2 | 258.3 | 1686.7 | 14 | K | 2 | 129.7 | 843.9 | 14 |
| P 3 | 355.4 | 1558.6 | 13 | P | 3 | 178.2 | 779.8 | 13 |
| S 4 | 442.5 | 1461.4 | 12 | S | 4 | 221.8 | 731.2 | 12 |
| T 5 | 543.6 | 1374.4 | 11 | T | 5 | 272.3 | 687.7 | 11 |
| D 6 | 658.7 | 1273.3 | 10 | D | 6 | 329.8 | 637.1 | 10 |
| P 7 | 755.8 | 1158.2 | 9 | P | 7 | 378.4 | 579.6 | 9 |
| L 8 | 869.0 | 1061.0 | 8 | L | 8 | 435.0 | 531.0 | 8 |
| *Y 9 | 1112.1 | 947.9 | 7 | *Y | 9 | 556.6 | 474.4 | 7 |
| D 10 | 1227.2 | 704.7 | 6 | D | 10 | 614.1 | 352.9 | 6 |
| T 11 | 1328.3 | 589.6 | 5 | T | 11 | 664.7 | 295.3 | 5 |
| P 12 | 1425.4 | 488.5 | 4 | P | 12 | 713.2 | 244.8 | 4 |
| D 13 | 1540.5 | 391.4 | 3 | D | 13 | 770.8 | 196.2 | 3 |
| T 14 | 1641.6 | 276.3 | 2 | T | 14 | 821.3 | 138.7 | 2 |
| R 15 | 1797.8 | 175.2 | 1 | R | 15 | 899.4 | 88.1 | 1 |

REAGENTS FOR THE DETECTION OF PROTEIN PHOSPHORYLATION IN C-SRC SIGNALING PATHWAYS

RELATED APPLICATIONS

This application claims the priority benefit of U.S. Ser. No. 10/777,893, filed Feb. 12, 2004 (now U.S. Pat. No. 7,300,753), and PCT/US04/26199 filed Aug. 12, 2004.

FIELD OF THE INVENTION

The invention relates generally to antibodies and peptide reagents for the detection of protein phosphorylation, and to protein phosphorylation in cancer.

BACKGROUND OF THE INVENTION

The activation of proteins by post-translational modification represents an important cellular mechanism for regulating most aspects of biological organization and control, including growth, development, homeostasis, and cellular communication. For example, protein phosphorylation plays a critical role in the etiology of many pathological conditions and diseases, including cancer, developmental disorders, autoimmune diseases, and diabetes. In spite of the importance of protein modification, it is not yet well understood at the molecular level. The reasons for this lack of understanding are, first, that the cellular modification system is extraordinarily complex, and second, that the technology necessary to unravel its complexity has not yet been fully developed.

The complexity of protein modification, including phosphorylation, on a proteome-wide scale derives from three factors: the large number of modifying proteins, e.g. kinases, encoded in the genome, the much larger number of sites on substrate proteins that are modified by these enzymes, and the dynamic nature of protein expression during growth, development, disease states, and aging. The human genome encodes, for example, over 520 different protein kinases, making them the most abundant class of enzymes known. See Hunter, *Nature* 411: 355-65 (2001). Each of these kinases phosphorylates specific serine, threonine, or tyrosine residues located within distinct amino acid sequences, or motifs, contained within different protein substrates. Most kinases phosphorylate many different proteins: it is estimated that one-third of all proteins encoded by the human genome are phosphorylated, and many are phosphorylated at multiple sites by different kinases. See Graves et al., *Pharmacol. Ther.* 82:111-21 (1999).

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Oncogenic kinases such as ErbB2 and Jak3, widely expressed in breast tumors and various leukemias, respectively, transform cells to the oncogenic phenotype at least in part because of their ability to phosphorylate cellular proteins. Understanding which proteins are modified by these kinases will greatly expand our understanding of the molecular mechanisms underlying oncogenic transformation. Thus, the ability to identify modification sites, e.g. phosphorylation sites, on a wide variety of cellular proteins is crucially important to understanding the key signaling proteins and pathways implicated in disease progression, for example cancer.

The efficient identification of protein phosphorylation sites relevant to disease has been aided by the recent development of a powerful new class of antibodies, called motif-specific, context-independent antibodies, which are capable of specifically binding short, recurring signaling motifs comprising one or more modified (e.g. phosphorylated) amino acids in many different proteins in which the motif recurs. See U.S. Pat. No. 6,441,140, Comb et al. Many of these powerful new antibodies are now available commercially. See CELL SIGNALING TECHNOLOGY, INC. 2003-04 Catalogue. More recently, a powerful new method for employing such motif-specific antibodies in immunoaffinity techniques coupled with mass spectrometric analysis to rapidly identify modified peptides from complex biological mixtures has been described. See U.S. Patent Publication No. 20030044848, Rush et al.). Such techniques will enable the rapid elucidation of protein activation and phosphorylation events underlying diseases, like cancer, that are driven by disruptions in signal transduction.

Human c-Src, a non-receptor tyrosine kinase, is one such signaling molecule that is over-expressed and activated in large number of human cancers. Increased c-Src activity has been demonstrated in a variety of human cancers, including breast, colon, pancreatic, ovarian, lung, esophogeal, and neural. See, e.g., Yeatman, *Nature Reviews* 4: 470-480 (2004); Irby et al., *Oncogene* 19: 5636-642 (2000). In addition to its role in regulating cell proliferation, c-Src contributes to later-stage metastatic potential of cells via effects on adhesion, invasion, and motility. See, e.g., Yeatman supra.

Human c-Src kinase activity is regulated via phosphorylation of two critical tyrosine residues, Tyr419 and Tyr530. Autophosphorylation at Tyr419 in the SH1 kinase domain is required for full c-Src activity. Tyr530 in the c-terminal tail is involved in the down-regulation of c-Src. Phosphorylation of Tyr530 leads to a conformational change involving C-terminal binding to the SH2 domain, which results in diminished substrate access to the catalytic kinase domain and thus, reduced c-Src activity. See Yeatman, supra; Irby et al., supra. Accordingly, phosphatases that de-phosphorylate c-Src at the regulatory Tyr530 site can activate this kinase even at normal expression levels.

It is known that c-Src can be activated by a number of upstream receptor tyrosine kinases, including EGFR, PDGFR, ERBB2, and FGFR, among others, and interactions with these ligand-activated receptors can lead to synergistic c-SRC activation. Additionally, a number of downstream signaling protein targets of activated c-Src have been identified as potentially involved in mediating cellular transformation, including FAK (itself a non-receptor tyrosine kinase involved in regulating cell-cycle progression, survival, and migration), p190 RhoGAP, p120 RasGAP, and cortactin, whose association with, and/or phosphorylation by c-Src leads to cellular adhesion disassembly. See Yeatman, supra; Irby et al., supra. ERK is also a target of c-Src/FAK signaling, and its phosphorylation results in activation of MLCK, which contributes to adhesion disassembly. See Yeatman, supra. Activated c-Src is known to activate the transcription factor, STAT3. See Irby et al., supra. It is also believed that c-Src activation impacts metalloproteinase function, and hence the invasive potential of cells, via the c-JUN kinase signaling pathway. c-Src also induces VEGF activity, leading to enhanced angiogenesis. See Irby et al, supra.

However, despite the identification of some of the downstream targets of c-Src, the molecular mechanisms contributing to c-Src-mediated oncogenesis in a variety of human cancers remain incompletely understood. See Yeatman, supra. Indeed, while interest in c-Src as a therapeutic target has recently increased—Wyeth (SKI-606), Sugen (SU6656), and Ariad Pharmaceuticals (AP23464 and AP 23451) each have c-Src inhibitors in pre-clinical or Phase I clinical trials— the efficacy, mechanism of action, and clinical utility of these compounds in mediating molecular effects downstream of c-Src remain to be seen.

A few tyrosine phosphorylation sites on signaling proteins downstream of c-Src have been reported, including the non-receptor tyrosine kinase FAK, the adaptor proteins p130 CAS and Sam68, the actin binding protein cortactin, the phospholipid binding protein annexin A2 and the STAM interacting protein Hrs. See Calalb et al., *Mol. Cell. Biol.* 15: 954-963 (1995); Belsches et al., *Front. Biosci.* 2: d501-518 (1997); Bache et al., *Eur. J. Biochem* 269: 3881-3887 (1997); Schaller et al., *Mol. Cell. Biol.* 14: 1680-1688 (1994); Shen et al., *Oncogene* 18: 4647-4653 (1999). Nonetheless, the small number of c-Src signaling pathway-related phosphorylation sites that have been identified to date do not facilitate a complete and accurate understanding of how protein activation downstream of c-Src is driving the progression of cancers in which this kinase is activated.

Accordingly, there is a continuing need to unravel the molecular mechanisms of c-Src driven oncogenesis by identifying the downstream signaling proteins mediating cellular transformation in diseases involving activated c-Src. Identifying particular phosphorylation sites on such signaling proteins and providing new reagents, such as phospho-specific antibodies and AQUA peptides, to detect and quantify them remains particularly important to advancing our understanding of the biology of these cancers.

Presently, a handful of compounds targeting c-Src are in or entering clinical trials for the treatment of cancer. Although the activation and/or expression of c-Src itself can be detected, it is clear that other downstream effectors of c-Src signaling, having diagnostic, predictive, or therapeutic value, remain to be elucidated. Accordingly, identification of downstream signaling molecules and phospho-sites involved in the progression of c-Src driven cancers, and development of new reagents to detect and quantify these sites and proteins, may lead to improved diagnostic/prognostic markers, as well as novel drug targets, for the detection and treatment of these diseases.

SUMMARY OF THE INVENTION

The invention discloses 102 novel phosphorylation sites identified in signal transduction proteins and pathways downstream of c-Src, and provides new reagents, including phosphorylation-site specific antibodies and AQUA peptides, for the selective detection and quantification of these phosphorylated sites/proteins. Also provided are methods of using the reagents of the invention for the detection and quantification of the disclosed phosphorylation sites.

BRIEF DESCRIPTION OF THE DRAWINGS

FIG. 2—Is a table (corresponding to Table 1) enumerating the c-Src signaling protein phosphorylation sites disclosed herein: Column A=the abbreviated name of the parent protein; Column B=the full name of the parent protein; Column C=the SwissProt accession number for the protein (human sequence); Column D=the protein type/classification; Column F=the residue (in the parent protein amino acid sequence) at which phosphorylation occurs within the phosphorylation site; and Column G=the phosphorylation site sequence encompassing the phosphorylatable residue; (residue at which phosphorylation occurs (and corresponding to the respective entry in Column F) appears in lowercase.

DETAILED DESCRIPTION OF THE INVENTION

Figure 1:
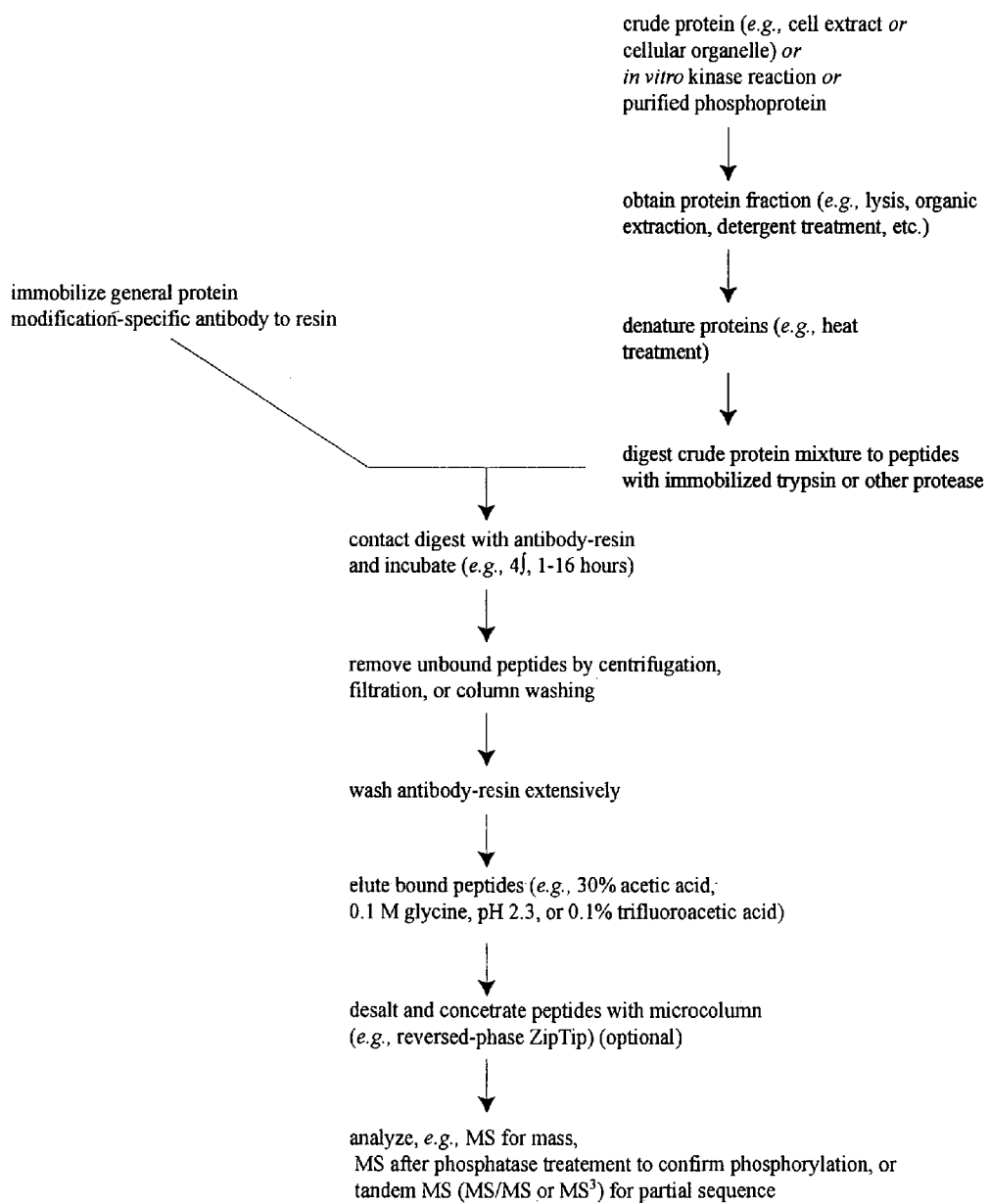
FIG. 1—Is a diagram broadly depicting the immunoaffinity isolation and mass-spectrometric characterization methodology (IAP) employed to identify the novel phosphorylation sites disclosed herein.
Figure 3:
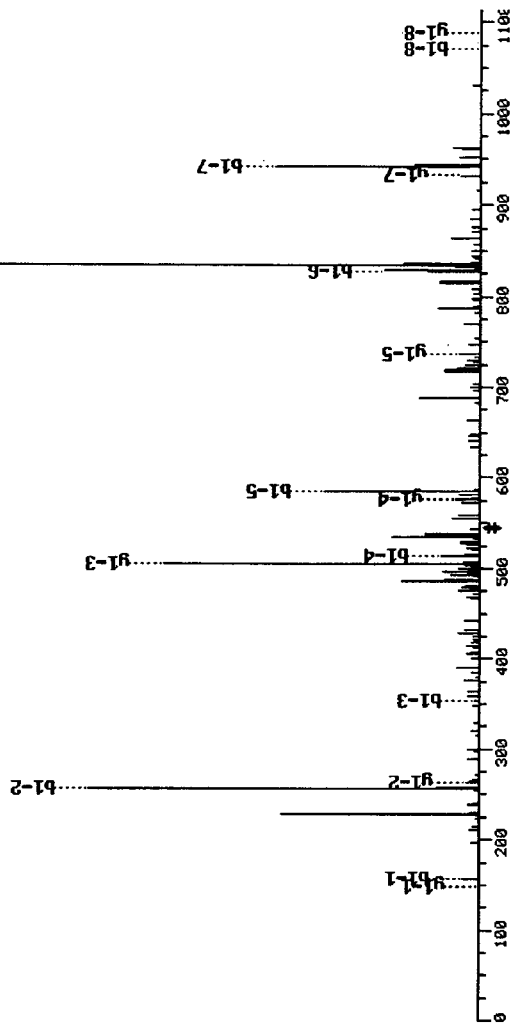
FIG. 3—is an exemplary mass spectrograph depicting the detection of the tyrosine 251 phosphorylation site in CrkL (see Row 15 in FIG. 2/Table 1), as further described in Example 1 (red and blue indicate ions detected in MS/MS spectrum).
Figure 4:
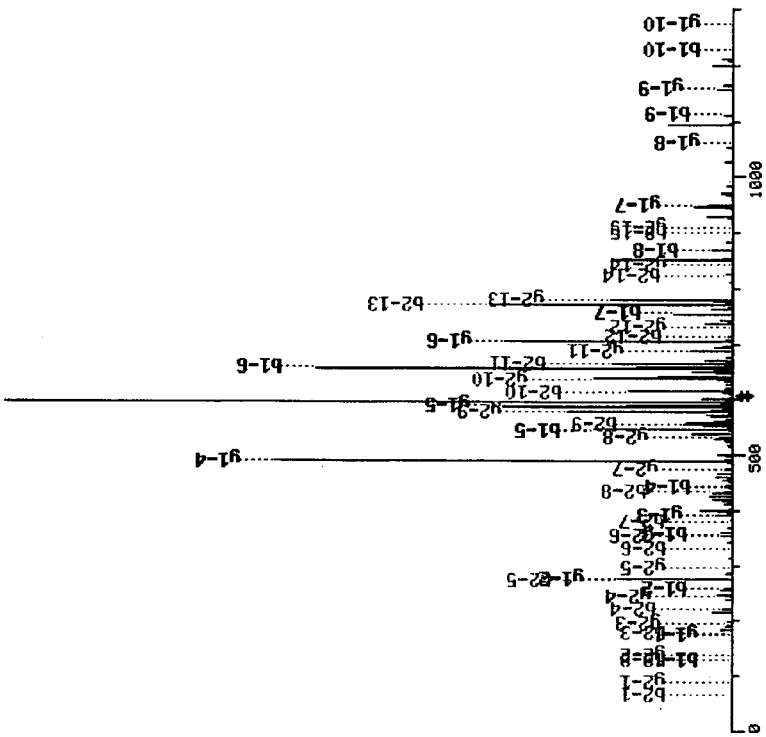
FIG. 4—is an exemplary mass spectrograph depicting the detection of the tyrosine 35 phosphorylation site in RIN1 (see Row 72 in FIG. 2/Table 1), as further described in Example 1 (red and blue indicate ions detected in MS/MS spectrum).
Figure 5:
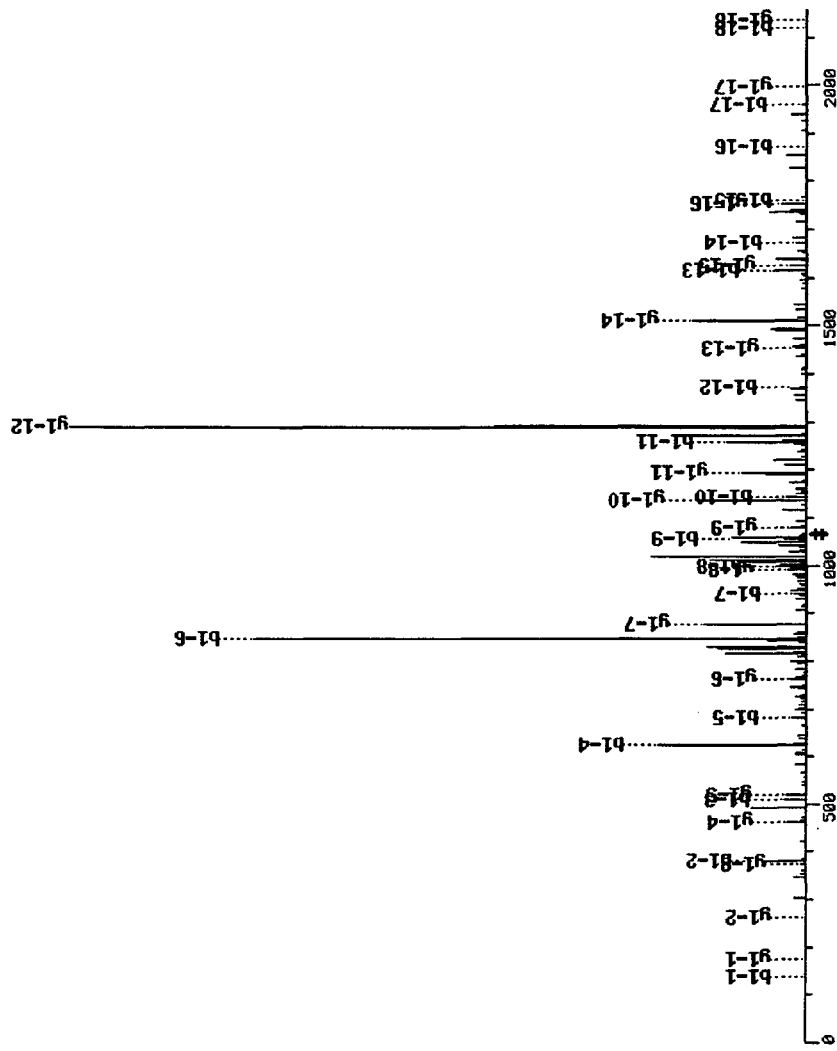
FIG. 5—is an exemplary mass spectrograph depicting the detection of the tyrosine 217 phosphorylation site in catenin delta-1 (see Row 3 in FIG. 2/Table 1), as further described in Example 1 (red and blue indicate ions detected in MS/MS spectrum).
Figure 6:
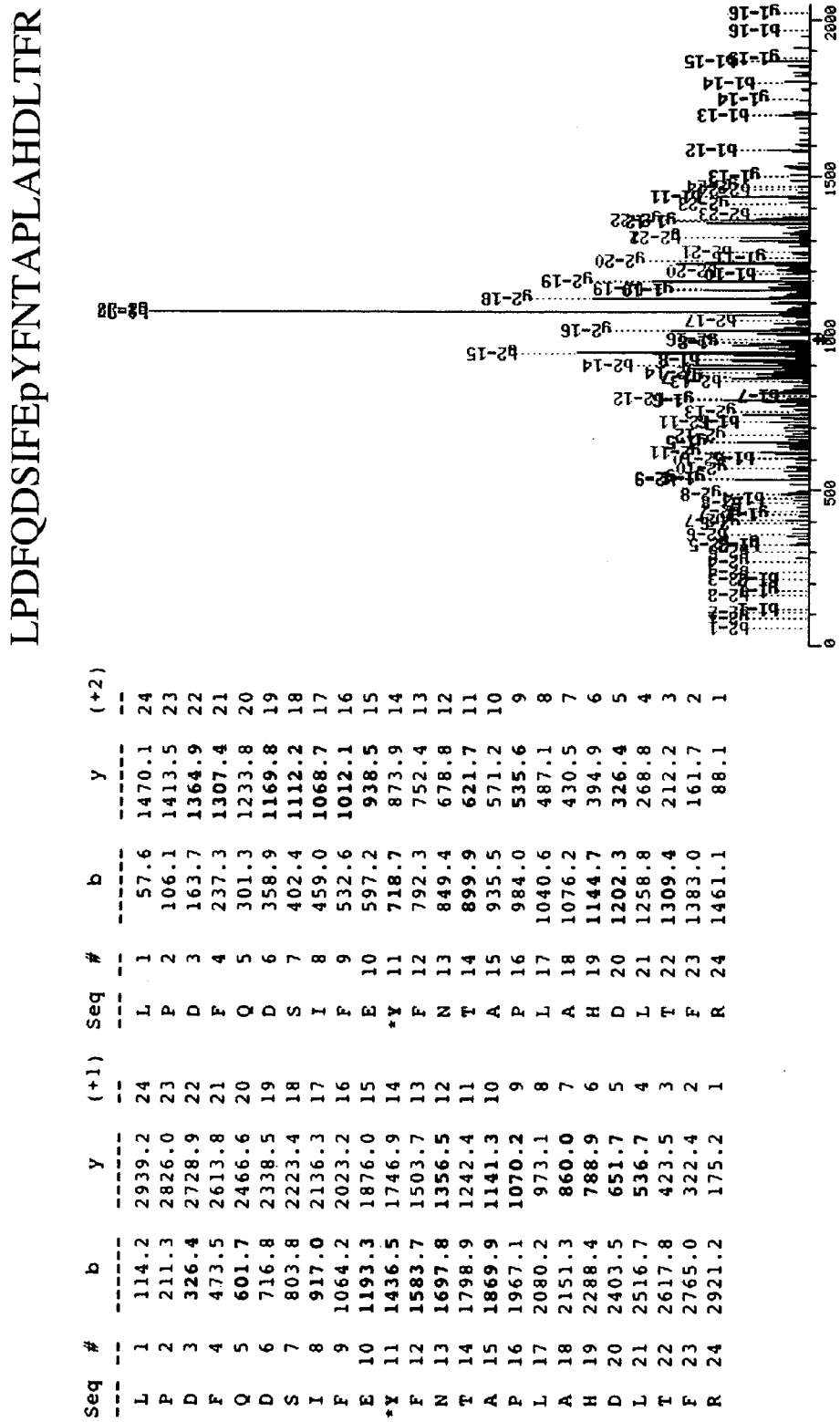
FIG. 6—is an exemplary mass spectrograph depicting the detection of the tyrosine 954 phosphorylation site in MRCK beta (see Row 80 in FIG. 2/Table 1), as further described in Example 1 (red and blue indicate ions detected in MS/MS spectrum).
Figure 7:
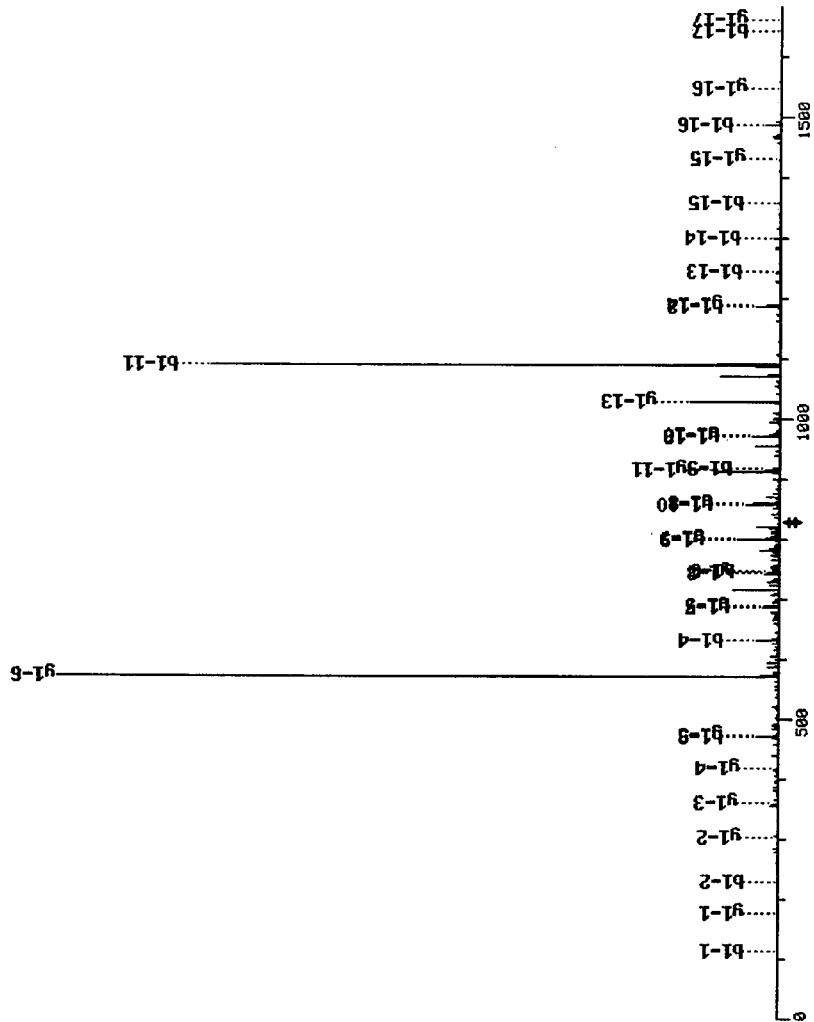
FIG. 7—is an exemplary mass spectrograph depicting the detection of the tyrosine 113 phosphorylation site in Shb (see Row 29 in FIG. 2/Table 1), as further described in Example 1 (red and blue indicate ions detected in MS/MS spectrum).

In accordance with the present invention, 102 novel protein phosphorylation sites in signaling proteins and pathways downstream of c-Src have now been discovered. These newly described phosphorylation sites were identified by employing the techniques described in "Immunoaffinity Isolation of Modified Peptides From Complex Mixtures," U.S. Patent Publication No. 20030044848, Rush et al., using cellular extracts from a stably-transfected cell line expressing constitutively activated mutant c-Src, as further described below. The novel phosphorylation sites, and their corresponding parent proteins, disclosed herein are listed in Table I. These phosphorylation sites correspond to numerous different parent proteins (the full sequences of which (human) are all publicly available in SwissProt database and their Accession numbers listed in Column C of Table 1/FIG. 2), each of which fall into discrete protein type groups, for example Adaptor/Scaffold proteins, GTPase Activating proteins, Helicases, and RNA Binding proteins, etc. (see Column D of Table 1), the phosphorylation of which is relevant to signal transduction activity downstream of c-Src, as disclosed herein.

The discovery of the 102 novel protein phosphorylation sites described herein enables the production, by standard methods, of new reagents, such as phosphorylation site-specific antibodies and AQUA peptides (heavy-isotope labeled peptides), capable of specifically detecting and/or quantifying these phosphorylated sites/proteins. Such reagents are highly useful, inter alia, for studying signal transduction events underlying the progression of c-Src mediated cancers. Accordingly, the invention provides novel reagents—phospho-specific antibodies and AQUA peptides—for the specific detection and/or quantification of a c-Src-related signaling protein/polypeptide only when phosphorylated (or only when not phosphorylated) at a particular phosphorylation site disclosed herein. The invention also provides methods of detecting and/or quantifying one or more phosphorylated c-Src-related signaling proteins using the phosphorylation-site specific antibodies and AQUA peptides of the invention.

In part, the invention provides an isolated phosphorylation site-specific antibody that specifically binds a given c-Srcrelated signaling protein only when phosphorylated (or not phosphorylated, respectively) at a particular tyrosine enumerated in Column F of Table 1/FIG. 2 comprised within the phosphorylatable peptide site sequence enumerated in corresponding Column G. In further part, the invention provides a heavy-isotope labeled peptide (AQUA peptide) for the quantification of a given c-Src-related signaling protein, the labeled peptide comprising a particular phosphorylatable peptide site/sequence enumerated in Column G of Table 1/FIG. 2 herein. For example, among the reagents provided by the invention is an isolated phosphorylation site-specific antibody that specifically binds the Cdc42 BP kinase beta protein (MRCK-beta) only when phosphorylated (or only when not phosphorylated) at tyrosine 954 (see Row 81 (and Columns F and G) of Table 1/FIG. 2). By way of further example, among the group of reagents provided by the invention is an AQUA peptide for the quantification of phosphorylated MRCK-beta, the AQUA peptide comprising the phosphorylatable peptide sequence listed in Column G, Row 81, of Table 1/FIG. 2.

In one embodiment, the invention provides an isolated phosphorylation site-specific antibody that specifically binds a human cellular-Src kinase (c-Src)-related signaling protein selected from Column A of Table 1 only when phosphorylated at the tyrosine listed in corresponding Column F of Table 1, comprised within the peptide sequence listed in corresponding Column G of Table 1 (SEQ ID NOs: 1-102), wherein said antibody does not bind said signaling protein when not phosphorylated at said tyrosine. In another embodiment, the invention provides an isolated phosphorylation site-specific antibody that specifically binds an c-Src-related signaling protein selected from Column A of Table 1 only when not phosphorylated at the tyrosine listed in corresponding Column F of Table 1, comprised within the peptide sequence listed in corresponding Column G of Table 1 (SEQ ID NOs: 1-102), wherein said antibody does not bind said signaling protein when phosphorylated at said tyrosine. Such reagents enable the specific detection of phosphorylation (or non-phosphorylation) of a novel phosphorylatable site disclosed herein. The invention further provides immortalized cell lines producing such antibodies. In one preferred embodiment, the immortalized cell line is a rabbit or mouse hybridoma.

In another embodiment, the invention provides a heavy-isotope labeled peptide (AQUA peptide) for the quantification of an c-Src-related signaling protein selected from Column A of Table 1, said labeled peptide comprising the phosphorylatable peptide sequence listed in corresponding Column G of Table 1 (SEQ ID NOs: 1-102), which sequence comprises the phosphorylatable tyrosine listed in corresponding Column F of Table 1. In certain preferred embodiments, the phosphorylatable tyrosine within the labeled peptide is phosphorylated, while in other preferred embodiments, the phosphorylatable tyrosine within the labeled peptide is not phosphorylated.

Reagents (antibodies and AQUA peptides) provided by the invention may conveniently be grouped by the type of c-Src-related signaling protein in which a given phosphorylation site (for which reagents are provided) occurs. The protein types for each respective protein (in which a phosphorylation site has been discovered) are provided in Column D of Table 1/FIG. 2, and include: Actin Binding proteins, Adaptor/Scaffold proteins, Adhesion proteins, Calcium-binding proteins, Cell Cycle Regulation proteins, Cell Surface proteins, Chaperones, Cytoskeletal proteins, Cellular Metabolism Enzymes, G protein or GTPase Activating proteins, Guanine Nucleotide Exchange Factors, Helicases, Immunoglobulin Superfamily proteins, Kinases, Ligases, Motor proteins, Protein Kinases, Protein Phosphatases, Receptor proteins, Ribosomal proteins, RNA Binding proteins, Transcription Factor/initiation Complex proteins, Translation Initiation Complex proteins, Ubitquitin Conjugating System proteins, and Vesicle proteins. Each of these distinct protein groups is considered a preferred subset of c-Src-related signal transduction protein phosphorylation sites disclosed herein, and reagents for their detection/quantification may be considered a preferred subset of reagents provided by the invention.

Particularly preferred subsets of the phosphorylation sites (and their corresponding proteins) disclosed herein are those occurring on the following protein types/groups listed in Column D of Table 1/FIG. 2: Adaptor/Scaffold proteins, Actin Binding proteins, Cytoskeletal proteins, G protein/GTPase Activating protein/Guanine Nucleotide Exchange Factor proteins, Helicases, RNA Binding proteins, Transcription/Translation Factor or Initiation Complex proteins, Cellular Metabolism Enzymes, and Vesicle proteins. Accordingly, among preferred subsets of reagents provided by the invention are isolated antibodies and AQUA peptides useful for the detection and/or quantification of the foregoing preferred protein/phosphorylation site subsets, as well as for the following preferred protein phosphorylation sites: NEDD5 (Y17), P13K p85-beta (Y458), MRCK-beta (Y954), MYPT1 (Y764), PTP-delta (Y666, Y667), RAIG1 (Y346, Y349), RPL3 (Y306), and Mahogunin (Y389, Y394).

In one subset of preferred embodiments, there is provided:
(i) An isolated phosphorylation site-specific antibody that specifically binds a an Adaptor/Scaffold protein selected from Column A, Rows 14-37, of Table 1 only when phosphorylated at the tyrosine listed in corresponding Column F, Rows 14-37, of Table 1, comprised within the phosphorylatable peptide sequence listed in corresponding Column G, Rows 14-37, of Table 1 (SEQ ID NOs: 13-36), wherein said antibody does not bind said protein when not phosphorylated at said tyrosine.
(ii) An equivalent antibody to (i) above that only binds the Adaptor/Scaffold protein when not phosphorylated at the disclosed site (and does not bind the protein when it is phosphorylated at the site).
(iii) A heavy-isotope labeled peptide (AQUA peptide) for the quantification of a an Adaptor/Scaffold protein selected from Column A, Rows 14-37, said labeled peptide comprising the phosphorylatable peptide sequence listed in corresponding Column G, Rows 14-37, of Table 1 (SEQ ID NOs: 13-36), which sequence comprises the phosphorylatable tyrosine listed in corresponding Column F, Rows 14-37, of Table 1.

Among this preferred subset of reagents, antibodies and AQUA peptides for the detection/quantification of the following Adaptor/Scaffold protein phosphorylation sites are particularly preferred: Cbl-b (Y1014), CrkL (Y251), DAB2 (Y342), Dok1 (Y336, Y340, Y401), P130Cas (Y228, Y366, Y376), and Shb (Y113) (see SEQ ID NOS: 13-18, 22-24, and 28).

In a second subset of preferred embodiments there is provided:
(i) An antibody that specifically binds an Actin Binding protein selected from Column A, Rows 2-13, of Table 1 only when phosphorylated at the tyrosine listed in corresponding Column F, Rows 2-13, of Table 1, comprised within the phosphorylatable peptide sequence listed in corresponding Column G, Rows 2-13, of Table 1 (SEQ ID NOS: 1-12), wherein said antibody does not bind said protein when not phosphorylated at said tyrosine.

(ii) An equivalent antibody to (i) above that only binds the Actin Binding protein when not phosphorylated at the disclosed site (and does not bind the protein when it is phosphorylated at the site).

(iii) A heavy-isotope labeled peptide (AQUA peptide) for the quantification of an Actin Binding protein selected from Column A, Rows 2-13, said labeled peptide comprising the phosphorylatable peptide sequence listed in corresponding Column G, Rows 2-13, of Table 1 (SEQ ID NOS: 1-12), which sequence comprises the phosphorylatable tyrosine listed in corresponding Column F, Rows 2-13, of Table 1.

Among this preferred subset of reagents, antibodies and AQUA peptides for the detection/quantification of the following Actin Binding protein phosphorylation sites are particularly preferred: Catenin delta-1 (Y217, Y221, Y257, Y280, Y334, Y96) (see SEQ ID NOs: 2-7).

In another subset of preferred embodiments there is provided:

(i) An isolated phosphorylation site-specific antibody that specifically binds a Cytoskeletal protein selected from Column A, Rows 47-59, of Table 1 only when phosphorylated at the tyrosine listed in corresponding Column F, Rows 47-59, of Table 1, comprised within the phosphorylatable peptide sequence listed in corresponding Column G, Rows 47-59, of Table 1 (SEQ ID NOs: 46-58), wherein said antibody does not bind said protein when not phosphorylated at said tyrosine.

(ii) An equivalent antibody to (i) above that only binds the Cytoskeletal protein when not phosphorylated at the disclosed site (and does not bind the protein when it is phosphorylated at the site).

(iii) A heavy-isotope labeled peptide (AQUA peptide) for the quantification of a a Cytoskeletal protein selected from Column A, Rows 47-59, said labeled peptide comprising the phosphorylatable peptide sequence listed in corresponding Column G, Rows 47-59, of Table 1 (SEQ ID NOs: 46-58), which sequence comprises the phosphorylatable tyrosine listed in corresponding Column F, Rows 47-59, of Table 1.

Among this preferred subset of reagents, antibodies and AQUA peptides for the detection/quantification of the following Cytoskeletal protein phosphorylation sites are particularly preferred: Talin-1 (Y1116), Vimentin (Y52, Y60), and Cortactin (Y215) (see SEQ ID NOs: 55-58).

In still another subset of preferred embodiments there is provided:

(i) An isolated phosphorylation site-specific antibody that specifically binds a G protein/GTPase Activating protein/Guanine Nucleotide Exchange Factor protein selected from Column A, Rows 65-73, of Table 1 only when phosphorylated at the tyrosine listed in corresponding Column F, Rows 65-73, of Table 1, comprised within the phosphorylatable peptide sequence listed in corresponding Column G, Rows 65-73, of Table 1 (SEQ ID NOs: 64-72), wherein said antibody does not bind said protein when not phosphorylated at said tyrosine.

(ii) An equivalent antibody to (i) above that only binds the G protein/GTPase Activating protein/Guanine Nucleotide Exchange Factor protein when not phosphorylated at the disclosed site (and does not bind the protein when it is phosphorylated at the site).

(iii) A heavy-isotope labeled peptide (AQUA peptide) for the quantification of a G protein/GTPase Activating protein/Guanine Nucleotide Exchange Factor protein selected from Column A, Rows 65-73, said labeled peptide comprising the phosphorylatable peptide sequence listed in corresponding Column G, Rows 65-73, of Table 1 (SEQ ID NOs: 64-72), which sequence comprises the phosphorylatable tyrosine listed in corresponding Column F, Rows 65-73, of Table 1.

Among this preferred subset of reagents, antibodies and AQUA peptides for the detection/quantification of the following G protein/GTPase Activating protein/Guanine Nucleotide Exchange Factor protein phosphorylation sites are particularly preferred: Rab7 (Y183), RasGAP3 (Y765), and Rin1 (Y35) (see SEQ ID NOs: 64, 70, and 71).

In still another subset of preferred embodiments there is provided:

(i) An isolated phosphorylation site-specific antibody that specifically binds a Helicase selected-from Column A, Rows 74-76, of Table 1 only when phosphorylated at the tyrosine listed in corresponding Column F, Rows 74-76, of Table 1, comprised within the phosphorylatable peptide sequence listed in corresponding Column G, Rows 74-76 of Table 1 (SEQ ID NOs: 73-75), wherein said antibody does not bind said protein when not phosphorylated at said tyrosine.

(ii) An equivalent antibody to (i) above that only binds the Helicase when not phosphorylated at the disclosed site (and does not bind the protein when it is phosphorylated at the site).

(iii) A heavy-isotope labeled peptide (AQUA peptide) for the quantification of a Helicase selected from Column A, Rows 74-76, said labeled peptide comprising the phosphorylatable peptide sequence listed in corresponding Column G, Rows 74-76, of Table 1 (SEQ ID NOs: 73-75), which sequence comprises the phosphorylatable tyrosine listed in corresponding Column F. Rows 74-76, of Table 1.

In yet another subset of preferred embodiments, there is provided:

(i) An isolated phosphorylation site-specific antibody that specifically binds an RNA Binding protein selected from Column A, Rows 87-89, of Table 1 only when phosphorylated at the tyrosine listed in corresponding Column F, Rows 87-89, of Table 1, comprised within the phosphorylatable peptide sequence listed in corresponding Column G, Rows 87-89, of Table 1 (SEQ ID NOs: 86-88), wherein said antibody does not bind said protein when not phosphorylated at said tyrosine.

(ii) An equivalent antibody to (i) above that only binds the RNA Binding protein when not phosphorylated at the disclosed site (and does not bind the protein when it is phosphorylated at the site).

(iii) A heavy-isotope labeled peptide (AQUA peptide) for the quantification of an c-Src-related signaling protein that is an RNA Binding protein selected from Column A, Rows 87-89, said labeled peptide comprising the phosphorylatable peptide sequence listed in corresponding Column G, Rows 87-89, of Table 1 (SEQ ID NOs: 86-88), which sequence comprises the phosphorylatable tyrosine listed in corresponding Column F, Rows 87-89, of Table 1.

In yet another subset of preferred embodiments, there is provided:

(i) An isolated phosphorylation site-specific antibody specifically binds a Transcription/Translation Factor or Initiation Complex protein selected from Column A, Rows 90-95, of Table 1 only when phosphorylated at the tyrosine listed in corresponding Column F, Rows 90-95, of Table 1, comprised within the phosphorylatable peptide sequence listed in corresponding Column G, Rows 90-95, of Table 1 (SEQ ID NOs: 89-94), wherein said antibody does not bind said protein when not phosphorylated at said tyrosine.

(ii) An equivalent antibody to (i) above that only binds the Transcription/Translation Factor or Initiation Complex protein when not phosphorylated at the disclosed site (and does not bind the protein when it is phosphorylated at the site).

(iii) A heavy-isotope labeled peptide (AQUA peptide) for the quantification of an c-Src-related signaling protein that is an Transcription/Translation Factor or Initiation Complex protein selected from Column A, Rows 90-95, said labeled peptide comprising the phosphorylatable peptide sequence listed in corresponding Column G, Rows 90-95, of Table 1 (SEQ ID NOs: 89-94), which sequence comprises the phosphorylatable tyrosine listed in corresponding Column F, Rows 90-95, of Table 1.

Among this preferred subset of reagents, antibodies and AQUA peptides for the detection/quantification of the following Transcription/Translation Factor or Initiation Complex protein phosphorylation sites are particularly preferred: eIF4H (Y12, Y45) (see SEQ ID NOs: 93 and 94).

In yet another subset of preferred embodiments, there is provided:
(i) An isolated phosphorylation site-specific antibody that specifically binds an a Cellular Metabolism Enzyme selected from Column A, Rows 60-64, of Table 1 only when phosphorylated at the tyrosine listed in corresponding Column F, Rows 60-64, of Table 1, comprised within the phosphorylatable peptide sequence listed in corresponding Column G, Rows 60-64, of Table 1 (SEQ ID NOs: 59-63), wherein said antibody does not bind said protein when not phosphorylated at said tyrosine.
(ii) An equivalent antibody to (i) above that only binds the Cellular Metabolism protein when not phosphorylated at the disclosed site (and does not bind the protein when it is phosphorylated at the site).
(iii) A heavy-isotope labeled peptide (AQUA peptide) for the quantification of an c-Src-related signaling protein that is a Cellular Metabolism Enzyme selected from Column A, Rows 60-64, said labeled peptide comprising the phosphorylatable peptide sequence listed in corresponding Column G, Rows 60-64, of Table 1 (SEQ ID NOs: 59-63), which sequence comprises the phosphorylatable tyrosine listed in corresponding Column F, Rows 60-64, of Table 1.

Among this preferred subset of reagents, antibodies and AQUA peptides for the detection/quantification of the following Cellular Metabolism Enyzme phosphorylation sites are particularly preferred: G6PD-2 (Y506), and GAPDH (Y315) (see SEQ ID NOs: 60 and 61).

In still another subset of preferred embodiments, there is provided:
(i) An isolated phosphorylation site-specific antibody that specifically binds a Vesicle protein selected from Column A, Rows 98-103, of Table 1 only when phosphorylated at the tyrosine listed in corresponding Column F, Rows 98-103, of Table 1, comprised within the phosphorylatable peptide sequence listed in corresponding Column G, Rows 98-103, of Table 1 (SEQ ID NOs: 97-102), wherein said antibody does not bind said protein when not phosphorylated at said tyrosine.
(ii) An equivalent antibody to (i) above that only binds the Vesicle protein when not phosphorylated at the disclosed site (and does not bind the protein when it is phosphorylated at the site).
(iii) A heavy-isotope labeled peptide (AQUA peptide) for the quantification of an c-Src-related signaling protein that is a Vesicle protein selected from Column A, Rows 98-103, said labeled peptide comprising the phosphorylatable peptide sequence listed in corresponding Column G, Rows 98-103, of Table 1 (SEQ ID NOs: 97-102), which sequence comprises the phosphorylatable tyrosine listed in corresponding Column F, Rows 98-103, of Table 1.

Among this preferred subset of reagents, antibodies and AQUA peptides for the detection/quantification of the following Vesicle protein phosphorylation sites are particularly preferred: Clathrin heavy chain 1 (Y910), and Dynamin-1 (Y354) (see SEQ ID NOs: 97 and 102).

In yet a further subset of preferred embodiments, there is provided:
(i) An isolated phosphorylation site-specific antibody that specifically binds a protein selected from the group consisting of NEDD5, P13K p85-beta, MRCK-beta, MYPT1, PTP-delta, RAIG1, RPL3, and Mahogunin (Column A, Rows 42, 78, 80-86, and 96-97 of Table 1) only when phosphorylated at the tyrosine listed in corresponding Column F, Rows 42, 78, 80-86, and 96-97 of Table 1), said tyrosine comprised within the phosphorylatable peptide sequence listed in corresponding Column G, Rows 42, 78, 80-86, and 96-97, of Table 1 (SEQ ID NOs: 41, 77, 79-85, and 95-96), wherein said antibody does not bind said protein when not phosphorylated at said tyrosine.
(ii) An equivalent antibody to (i) above that only binds the NEDD5, P13K p85-beta, MRCK-beta, MYPT1, PTP-delta, RAIG1, RPL3, and Mahogunin protein when not phosphorylated at the disclosed site (and does not bind the protein when it is phosphorylated at the site).
(iii) A heavy-isotope labeled peptide (AQUA peptide) for the quantification of a protein selected from the group consisting of NEDD5, P13K p85-beta, MRCK-beta, MYPT1, PTP-delta, RAIG1, RPL3, and Mahogunin (Column A, Rows 42, 78, 80-86, and 96-97 of Table 1), said labeled peptide comprising the phosphorylatable peptide sequence listed in corresponding Column G, Rows 42, 78, 80-86, and 96-97, of Table 1 (SEQ ID NOs: 41, 77, 79-85, and 95-96), which sequence comprises the phosphorylatable tyrosine listed in corresponding Column F, Rows 42, 78, 80-86, and 96-97, of Table 1.

The invention also provides, in part, an immortalized cell line producing an antibody of the invention, for example, a cell line producing an antibody within any of the foregoing preferred subsets of antibodies. In one preferred embodiment, the immortalized cell line is a rabbit hybridoma or a mouse hybridoma.

In certain other preferred embodiments, a heavy-isotope labeled peptide (AQUA peptide) of the invention (for example, an AQUA peptide within an of the foregoing preferred subsets of AQUA peptides) comprises a disclosed site sequence wherein the phosphorylatable tyrosine is phosphorylated. In certain other preferred embodiments, a heavy-isotope labeled peptide of the invention comprises a disclosed site sequence wherein the phosphorylatable tyrosine is not phosphorylated.

The foregoing subsets of preferred reagents of the invention should not be construed as limiting the scope of the invention, which, as noted above, includes reagents for the detection and/or quantification of disclosed phosphorylation sites on any of the other protein type/group subsets (each a preferred subset) listed in Column D of Table 1/FIG. 2.

Also provided by the invention are methods for detecting or quantifying a c-Src kinase-related signaling protein that is tyrosine-phosphorylated, said method comprising the step of utilizing one or more of the above-described reagents of the invention to detect or quantify one or more c-Src-related signaling protein(s) selected from Column A of Table 1 only when phosphorylated at the tyrosine listed in corresponding Column F of Table 1. In certain preferred embodiments of the methods of the invention, the reagents comprise a subset of preferred reagents as described above.

The identification of the disclosed novel c-Src-related signaling protein phosphorylation sites, and the standard production and use of the reagents provided by the invention are described in further detail below and in the Examples that follow.

All cited references are hereby incorporated herein, in their entirety, by reference. The Examples are provided to further illustrate the invention, and do not in any way limit its scope, except as provided in the claims appended hereto.

TABLE 1

Newly-Discovered c-Src-Related Phosphorylation Sites.

| | A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|---|
| 2 | anillin | Q8K298 | Actin binding protein | Y666 | SEDRDLLySIDAYRS | SEQ ID NO: 1 |
| 3 | catenin, delta-1 | P30999 | Actin binding protein | Y217 | PDGYGRHyEDGYPGG | SEQ ID NO: 2 |
| 4 | catenin, delta-1 | P30999 | Actin binding protein | Y221 | GRHYEDGyPGGSDNY | SEQ ID NO: 3 |
| 5 | catenin, delta-1 | P30999 | Actin binding protein | Y257 | APSRQDVyGPQPQVR | SEQ ID NO 4 |
| 6 | catenin, delta-1 | P30999 | Actin binding protein | Y280 | HRFHPEPyGLEDDQR | SEQ ID NO 5 |
| 7 | catenin, delta-1 | P30999 | Actin binding protein | Y334 | EEVPPDQyYWAPLAQ | SEQ ID NO 6 |
| 8 | catenin, delta-1 | P30999 | Actin binding protein | Y96 | QDHNHLLySTIPRMQ | SEQ ID NO 7 |
| 9 | Filamin B | Q80X90 | Actin binding protein | Y2502 | RSSTETCySAIPKSS | SEQ ID NO: 8 |
| 10 | IRSp53 | Q91V97 | Actin binding protein | Y338 | QSKLSDSySNTLPVR | SEQ ID NO: 9 |
| 11 | IRSp53 | Q91V97 | Actin binding protein | Y492 | GTFKQRPySVAVPAF | SEQ ID NO: 10 |
| 12 | IRSp53 | Q91V97 | Actin binding protein | Y506 | FSQGLDDyGARSVSR | SEQ ID NO: 11 |
| 13 | tensin 2 | Q8CJ95 | Actin binding protein | Y460 | GPLDGSPyAQVQRVP | SEQ ID NO: 12 |
| 14 | Cbl-b | P70451 | Adaptor/scaffold | Y1014 | ASQDyDQLPSSSD | SEQ ID NO: 13 |
| 15 | CrkL | P47941 | Adaptor/scaffold | Y251 | QKRVPCAyDKTALAL | SEQ ID NO: 14 |
| 16 | DAB2 | P98078 | Adaptor/scaffold | Y342 | PLNVDTDyFGQQFDQ | SEQ ID NO: 15 |
| 17 | Dok1 | P97465 | Adaptor/scaffold | Y336 | VHSKKPLyWDLYGHV | SEQ ID NO: 16 |
| 18 | Dok1 | P97465 | Adaptor/scaffold | Y340 | KPLYWDLyGHVQQQL | SEQ ID NO: 17 |
| 19 | Dok1 | P97465 | Adaptor/scaffold | Y401 | EEGYELPyNPATDDY | SEQ ID NO: 18 |
| 20 | Eps8 | Q08509 | Adaptor/scaffold | Y490 | DYPPADGyAYSSSMY | SEQ ID NO: 19 |
| 21 | Eps8 | Q08509 | Adaptor/scaffold | Y492 | PPADGYAySSSMYHR | SEQ ID NO: 20 |
| 22 | LIM | Q9QYN2 | Adaptor/scaffold | Y251 | VERNTEFyHIPTHSD | SEQ ID NO: 21 |
| 23 | P130Cas | Q61140 | Adaptor/scaffold | Y228 | RVGQGYVyEAAQTEQ | SEQ ID NO: 22 |
| 24 | P130Cas | Q61140 | Adaptor/scaffold | Y366 | SPAAEDVyDVPPPAP | SEQ ID NO: 23 |
| 25 | P130Cas | Q61140 | Adaptor/scaffold | Y376 | PPPAPDLyDVPPGLR | SEQ ID NO: 24 |
| 26 | RA70 | Q9Z2K4 | Adaptor/scaffold | Y197 | CAPDKRIyQFTAASP | SEQ ID NO: 25 |
| 27 | RA70 | Q9Z2K4 | Adaptor/scaffold | Y260 | QPIDDEIyEELPEEE | SEQ ID NO: 26 |

TABLE 1-continued

Newly-Discovered c-Src-Related Phosphorylation Sites.

| | A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|---|
| 28 | RA70 | Q9Z2K4 | Adaptor/scaffold | Y75 | DAEDGDEyDDPFAGP | SEQ ID NO: 27 |
| 29 | Shb | XP_131399 | Adaptor/scaffold | Y113 | RAMCRLDyCGGGGGG | SEQ ID NO: 28 |
| 30 | tensin 1 | Q7TPM8 | Adaptor/scaffold | Y213 | SLDRHAAyGGYSTPE | SEQ ID NO: 29 |
| 31 | tensin 1 | Q7TPM8 | Adaptor/scaffold | Y216 | RHAAYGGySTPEDRR | SEQ ID NO: 30 |
| 32 | ZO1 | P39447 | Adaptor/scaffold | Y1164 | EEQPAPAyEVHNRYR | SEQ ID NO: 31 |
| 33 | ZO1 | P39447 | Adaptor/scaffold | Y1177 | YRPEAQPySSTGPKS | SEQ ID NO: 32 |
| 34 | ZO2 | Q9Z0U1 | Adaptor/scaffold | Y554 | VREDAVLyLLEIPKG | SEQ ID NO: 33 |
| 35 | LPP | Q8BFW7 | Adaptor/scaffold;<br>Cytoskeletal<br>protein | Y245 | GPSSGQIyGPGPRGY | SEQ ID NO: 34 |
| 36 | LPP | Q8BFW7 | Adaptor/scaffold;<br>Cytoskeletal<br>protein | Y301 | QGRYYEPyYAAGPSY | SEQ ID NO: 35 |
| 37 | EPS15R | Q60902 | Adaptor/scaffold;<br>Vesicle protein | Y562 | AHRSLEQyDQVPDGV | SEQ ID NO: 36 |
| 38 | protocadherin 7 | O88185 | Adhesion | Y948 | KKSKQPLySSIVTVE | SEQ ID NO: 37 |
| 39 | SREC-II | P59222 | Adhesion | Y615 | EGPSGALyARVARRE | SEQ ID NO: 38 |
| 40 | annexin A2 | P07356 | Calcium-<br>binding protein | Y23 | HSTPPSAyGSVKPYT | SEQ ID NO: 39 |
| 41 | annexin A2 | P07356 | Calcium-<br>binding protein | Y237 | RYKSYSPyDMLESIK | SEQ ID NO: 40 |
| 42 | NEDD5 | P42208 | Cell cycle<br>regulation | Y17 | INPETPGyVGFANLP | SEQ ID NO: 41 |
| 43 | septin 7 | O55131 | Cell cycle<br>regulation | Y318 | RKLAAVTyNGVDNNK | SEQ ID NO: 42 |
| 44 | CD34 | Q64314 | Cell surface | Y326 | ERLGEDPyYTENGGG | SEQ ID NO: 43 |
| 45 | CD34 | Q64314 | Cell surface | Y336 | ENGGGQGySSGPGAS | SEQ ID NO: 44 |
| 46 | HSC70 | P08109 | Chaperone | Y15 | GIDLGTTySCVGVFQ | SEQ ID NO: 45 |
| 47 | actin, beta | P70514 | Cytoskeletal<br>protein | Y166 | VTHTVPIyEGYALPH | SEQ ID NO: 46 |
| 48 | actin, gamma,<br>similar to | XP_13466<br>3 | Cytoskeletal<br>protein | Y53 | GMGQKDSyVGDKAQS | SEQ ID NO: 47 |
| 49 | actinin,<br>alpha 4 | P57780 | Cytoskeletal<br>protein | Y266 | MTYVSSFyHAFSGAQ | SEQ ID NO: 48 |
| 50 | DAL-1 | Q9WV92 | Cytoskeletal<br>protein | Y479 | AEVGTGQyATTKGIS | SEQ ID NO: 49 |
| 51 | ELMO2 | Q8BHL5 | Cytoskeletal<br>protein | Y48 | WSLPNPEyYTLRYAD | SEQ ID NO: 50 |
| 52 | EPB41L2 | O70318 | Cytoskeletal<br>protein | Y606 | RVDGDNIyVRHSNLM | SEQ ID NO: 51 |
| 53 | EPB41L2 | O70318 | Cytoskeletal<br>protein | Y889 | TETKTITyESPQIDG | SEQ ID NO: 52 |
| 54 | eplin | Q9ERG0 | Cytoskeletal<br>protein | Y746 | QIKRNRYyDEDEDEE | SEQ ID NO: 53 |

TABLE 1-continued

Newly-Discovered c-Src-Related Phosphorylation Sites.

| A<br>Protein Name<br>1 (short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 55 plectin 1 | XP_12827 7.4 | Cytoskeletal protein | Y3579 | SKGYYSPySVSGSGS | SEQ ID NO: 54 |
| 56 talin 1 | P26039 | Cytoskeletal protein | Y1116 | IAQGNENyAGIAARD | SEQ ID NO: 55 |
| 57 vimentin | P20152 | Cytoskeletal protein | Y52 | PSTSRSLySSSPGGA | SEQ ID NO: 56 |
| 58 vimentin | P20152 | Cytoskeletal protein | Y60 | SSSPGGAyVTRSSAV | SEQ ID NO: 57 |
| 59 cortactin | Q60598 | Cytoskeletal protein; Actin binding protein | Y215 | KSAVGFEyQGKTEKH | SEQ ID NO: 58 |
| 60 enolase, alpha | P17182 | Enzyme, cellular metabolism | Y24 | PTVEVDLyTAKGLFR | SEQ ID NO: 59 |
| 61 G6PD-2 | P97324 | Enzyme, cellular metabolism | Y506 | GFQYKGTyKGTHKH | SEQ ID NO: 60 |
| 62 GAPDH | P16858 | Enzyme, cellular metabolism | Y315 | ISWYDNEyGYSNRVV | SEQ ID NO: 61 |
| 63 phosphogly-cerate mutase 1 | Q9DBJ1 | Enzyme, cellular metabolism | Y25 | ENRFSGWyDADLSPA | SEQ ID NO: 62 |
| 64 similar to GAPDH | XP_19563 2 | Enzyme, cellular metabolism | Y154 | ISWYNNEyGYSNREE | SEQ ID NO: 63 |
| 65 Rab7 | P51150 | G protein, Rab | Y183 | QETEVELyNEEPEPI | SEQ ID NO: 64 |
| 66 centaurin-beta 2 | XP_19383 6.3 | GTPase activating protein, ARF | Y773 | MRESEGLyGQPGDET | SEQ ID NO: 65 |
| 67 GIT1 | XP_12629 1.5 | GTPase activating protein, ARF | Y562 | ELEDDAIySVHVPAG | SEQ ID NO: 66 |
| 68 GIT1 | XP_12629 1.5 | GTPase activating protein, ARF | Y571 | VHVPAGLyRIRKGVS | SEQ ID NO: 67 |
| 69 IQGAP1 | Q9JKF1 | GTPase activating protein, Ras | Y1510 | LVKLQQTySALNSKA | SEQ ID NO: 68 |
| 70 IQGAP1 | Q9JKF1 | GTPase activating protein, Ras | Y172 | APQIQDLyGKVDFTE | SEQ ID NO: 69 |
| 71 RasGAP 3 | Q60790 | GTPase activating protein, Ras | Y765 | DGPEQEEySTFVIDD | SEQ ID NO: 70 |
| 72 Rin1 | Q921Q7 | Guanine nucleotide exchange factor, Rab | Y35 | KPSTDPLyDTPDTRG | SEQ ID NO: 71 |
| 73 Tiam1 | Q60610 | Guanine nucleotide exchange factor, Rac/Rho | Y1323 | GSHRLSIyEEWDPFR | SEQ ID NO: 72 |

TABLE 1-continued

Newly-Discovered c-Src-Related Phosphorylation Sites.

| A<br>1 Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 74 DDX3 | Q62167 | Helicase | Y103 | DDRGRGDyDGIGGRG | SEQ ID NO: 73 |
| 75 DBY | Q9QWS9 | Helicase; RNA binding protein | Y104 | DDHGRNDyDGIGGRD | SEQ ID NO: 74 |
| 76 PL10 | P16381 | Helicase; RNA binding protein | Y67 | WSKDKDAySSFGSRS | SEQ ID NO: 75 |
| 77 TAGE4 | Q60977 | Immunoglobulin superfamily | Y398 | SERENVQySSVNGDC | SEQ ID NO: 76 |
| 78 PI3K p85-beta | O08908 | Kinase, lipid | Y458 | SREYDQLyEEYTRTS | SEQ ID NO: 77 |
| 79 glutamyl-prolyl-tRNA synthetase | Q8CGC7 | Ligase | Y690 | PYEPVSPySCREAPC | SEQ ID NO: 78 |
| 80 MRCK-beta | Q7TT50 | Protein kinase, Ser/Thr (non-receptor) | Y954 | FQDSIFEyFNTAPLA | SEQ ID NO: 79 |
| 81 MYPT1 | Q9DBR7 | Protein phosphatase, dual-specificity | Y764 | SRTYDETyTRYRPVS | SEQ ID NO: 80 |
| 82 RAIG1 | Q8BHL4 | Receptor, GPCR | Y346 | AQAPASPyNDYEGRK | SEQ ID NO: 81 |
| 83 RAIG1 | Q8BHL4 | Receptor, GPCR | Y349 | PASPYNDyEGRKGDS | SEQ ID NO: 82 |
| 84 PTP-delta | Q64487 | Receptor, protein phosphatase, tyrosine | Y666 | NSSDTTKyLLEQLEK | SEQ ID NO: 83 |
| 85 PTP-delta | Q64487 | Receptor, protein phosphatase, tyrosine | Y677 | QLEKWTEyRITVTAH | SEQ ID NO: 84 |
| 86 RPL3 | P27659 | Ribosomal protein | Y306 | KNNASTDyDLSDKSI | SEQ ID NO: 85 |
| 87 FXR1 | Q61584 | RNA binding protein | Y506 | KDPDSNPySLLDNTE | SEQ ID NO: 86 |
| 88 FXR2 | Q9WVR4 | RNA binding protein | Y520 | KDPDSNPySLLDTSE | SEQ ID NO: 87 |
| 89 RBM3 | O89086 | RNA binding protein | Y139 | YSGSQGGyDRYSGGN | SEQ ID NO: 88 |
| 90 ZNF289 | Q9D758 | Transcription factor | Y458 | GREVDSEyEARSRLQ | SEQ ID NO: 89 |
| 91 PTRF | O54724 | Transcription initiation complex | Y310 | FTPDHVVyARSKTAV | SEQ ID NO: 90 |
| 92 eIF3E | P60229 | Translation initiation complex | Y445 | ATQDSGFy | SEQ ID NO: 91 |
| 93 eEF1A-1 | P10126 | Translation initiation complex | Y29 | TTTGHLIyKCGGIDK | SEQ ID NO: 92 |
| 94 eIF4H | Q9WUK2 | Translation initiation complex | Y12 | DTYDDRAySSFGGGR | SEQ ID NO: 93 |

TABLE 1-continued
Newly-Discovered c-Src-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 95 eIF4H | Q9WUK2 | Translation initiation complex | Y45 | TEPPYTAyVGNLPFN | SEQ ID NO: 94 |
| 96 mahogunin | Q9D074 | Ubiquitin conjugating system | Y389 | AIPSAPLyEEITYSG | SEQ ID NO: 95 |
| 97 mahogunin | Q9D074 | Ubiquitin conjugating system | Y394 | PLYEEITySGISDGL | SEQ ID NO: 96 |
| 98 Clathrin heavy chain 1 | Q80U89 | Vesicle protein | Y910 | FLRENPYyDSRVVGK | SEQ ID NO: 97 |
| 99 Munc-18a | O08599 | Vesicle protein | Y473 | ERISEQTyQLSRWTP | SEQ ID NO: 98 |
| 100 SH3 domain protein 28 | Q62419 | Vesicle protein | Y315 | QPSCKALyDFEPEND | SEQ ID NO: 99 |
| 101 sorting nexin 9 | Q91VH2 | Vesicle protein | Y239 | IAIVGDyGPMVVVYP | SEQ ID NO: 100 |
| 102 EHD1 | Q9WVK4 | Vesicle protein; calcium-binding protein | Y453 | PTYDEIFyTLSPVNG | SEQ ID NO: 101 |
| 103 dynamin-1 | P39053 | Vesicle protein | Y354 | SGDQIDTyELSGGAR | SEQ ID NO: 102 |

The short name for each protein in which a phosphorylation site has presently been identified is provided in Column A, and it accession number (human) is provided Column C. The protein type/group into which each protein falls is provided in Column D. The identified tyrosine residue at which phosphorylation occurs in a given protein is identified in Column F and the amino acid sequence of the phosphorylation site encompassing the tyrosine residue is provided in Column G (lower case y=the tyrosine (identified in Column F) at which phosphorylation occurs. Table 1 above is identical to FIG. 2, except that the latter includes the full protein name (Column B).

The identification of these 102 phosphorylation sites is described in more detail in Part A below and in Example 1.

Definitions

As used herein, the following terms have the meanings indicated:

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "does not bind" with respect to an antibody's binding to one phospho-form of a sequence means does not substantially react with as compared to the antibody's binding to the other phospho-form of the sequence for which the antibody is specific.

"c-Src-related signaling protein" means any protein (or polypeptide derived therefrom) enumerated in Column A of Table 1/FIG. 2, which is disclosed herein as being phosphorylated in one or more c-Src-activated cell line(s). c-Src related signaling proteins may be direct substrates of c-Src kinase, or may be indirect substrates downstream of c-Src in signaling pathways. A c-Src-related signaling protein may also be phosphorylated in other cell lines harboring activated kinase activity.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Protein" is used interchangeably with polypeptide, and includes protein fragments and domains as well as whole protein.

"Phosphorylatable amino acid" means any amino acid that is capable of being modified by addition of a phosphate group, and includes both forms of such amino acid.

"Phosphorylatable peptide sequence" means a peptide sequence comprising a phosphorylatable amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

A. Identification of Novel c-Src-Related Phosphorylation Sites.

The 102 novel c-Src-related signaling protein phosphorylation sites disclosed herein and listed in Table 1/FIG. 2 were discovered by employing the modified peptide isolation and characterization techniques described in described in "Immunoaffinity Isolation of Modified Peptides From Complex Mixtures," U.S. Patent Publication No. 20030044848, Rush et al. (the teaching of which is hereby incorporated herein by reference, in its entirety) using cellular extracts from a stably-transfected NIH/3T3 cell line expressing constitutively activated mutant c-Src (Y527F). The isolation and identification of phosphopeptides from this c-Src cell line, using an immobilized general phosphotyrosine-specific antibody, is described in detail in Example 1 below. In addition to the 102 previously unknown protein phosphorylation sites discovered, many known phosphorylation sites were also identified (not described herein). The immunoaffinity/mass spectrometric technique described in the '848 Patent Publication (the "IAP" method)—and employed as described in detail in the Examples—is briefly summarized below.

The IAP method employed generally comprises the following steps: (a) a proteinaceous preparation (e.g. a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g. Sequest) may be utilized to substantially match the spectra obtained for the isolated, modified peptide during the characterization of step (d) with the spectra for a known peptide sequence. A quantification step employing, e.g. SILAC or AQUA, may also be employed to quantify isolated peptides in order to compare peptide levels in a sample to a baseline.

In the IAP method as employed herein, a general phosphotyrosine-specific monoclonal antibody (commercially available from Cell Signaling Technology, Inc., Beverly, Mass., Cat #9411 (p-Tyr-100)) was used in the immunoaffinity step to isolate the widest possible number of phospho-tyrosine containing peptides from the c-Src cell extracts.

Extracts from a c-Src activated NIH/3T3 cell line was employed. This stably-transfected cell line expresses a constitutively activated mutant form of c-Src (Y527F), in which signaling pathways and proteins downstream of c-Src are affected.

As described in more detail in the Examples, lysates were prepared from this cell line and digested with trypsin after treatment with DTT and iodoacetamide to alkylate cysteine residues. Before the immunoaffinity step, peptides were prefractionated by reversed-phase solid phase extraction using Sep-Pak $C_{18}$ columns to separate peptides from other cellular components. The solid phase extraction cartridges were eluted with varying steps of acetonitrile. Each lyophilized peptide fraction was redissolved in PBS and treated with phosphotyrosine antibody (P-Tyr-100, CST#9411) immobilized on protein G-Sepharose. Immunoaffinity-purified peptides were eluted with 0.1% TFA and a portion of this fraction was concentrated with Stage tips and analyzed by LC-MS/MS, using a ThermoFinnigan LCQ Deca XP Plus ion trap mass spectrometer. Peptides were eluted from a 10 cm×75 µm reversed-phase column with a 45-min linear gradient of acetonitrile. MS/MS spectra were evaluated using the program Sequest with the NCBI human protein database.

This revealed a total of 102 novel tyrosine phosphorylation sites in signaling pathways affected by c-Src activation. The identified phosphorylation sites and their parent proteins are enumerated in Table 1/FIG. 2. The tyrosine (human sequence) at which phosphorylation occurs is provided in Column F, and the peptide sequence encompassing the phosphorylatable tyrosine residue at the site is provided in Column G.

As a result of the discovery of these phosphorylation sites, phospho-specific antibodies and AQUA peptides for the detection of and quantification of these sites and their parent proteins may now be produced by standard methods, described below. These new reagents will prove highly useful in studying the signaling pathways and events underlying the progression of c-Src-mediated cancers and the identification of new biomarkers and targets for diagnosis and treatment of such diseases.

B. Antibodies and Cell Lines

Isolated phosphorylation site-specific antibodies that specifically bind an c-Src-related signaling protein disclosed in Column A of Table 1 only when phosphorylated (or only when not phosphorylated) at the corresponding amino acid and phosphorylation site listed in Columns F and G of Table 1 may now be produced by standard antibody production methods, such as anti-peptide antibody methods, using the phosphorylation site sequence information provided in Column G of Table 1. For example, three previously unknown Dok1 phosphorylation sites (tyrosines 336, 340, and 401) (see Rows 17-19 of Table 1) are presently disclosed. Thus, antibodies that specifically bind any one of these novel Dok1 sites can now be produced by using (all or part on the amino acid sequence encompassing the respective phosphorylated residue as a peptide antigen used to immunize an animal (e.g. a peptide antigen comprising the sequence set forth in Row 17, Column G, of Table 1 (which encompasses the phosphorylated tyrosine at position 336 in Dok1) may be employed to produce an antibody that only binds Dok1 when phosphorylated at Tyr336).

Polyclonal antibodies of the invention may be produced according to standard techniques by immunizing a suitable animal (e.g., rabbit, goat, etc.) with a peptide antigen corresponding to the c-Src-related phosphorylation site of interest (i.e. a phosphorylation site enumerated in Column G of Table 1, which comprises the corresponding phosphorylatable amino acid listed in Column F of Table 1), collecting immune serum from the animal, and separating the polyclonal antibodies from the immune serum, in accordance with known procedures. For example, a peptide antigen comprising the novel Talin-1 phosphorylation site disclosed herein (SEQ ID NO: 55=IAQGNENyAGIMRD, encompassing phosphorylated tyrosine 1116 (see Row 56 of Table 1)) may be used to produce antibodies that only bind Talin-1 when phosphorylated at Tyr1116. Similarly, a peptide comprising any of the phosphorylation site sequences provided in Column G of Table 1 may employed as an antigen to produce an antibody that only binds the corresponding protein listed in Column A of Table 1 when phosphorylated (or when not phosphorylated) at the corresponding residue listed in Column F. If an antibody that only binds the protein when phosphorylated at the disclosed site is desired, the peptide antigen includes the phosphorylated form of the amino acid. Conversely, if an antibody that only binds the protein when not phosphorylated at the disclosed site is desired, the peptide antigen includes the non-phosphorylated form of the amino acid.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)).

It will be appreciated by those of skill in the art that longer or shorter phosphopeptide antigens may be employed. See Id. For example, a peptide antigen may consist of the full sequence disclosed in Column G of Table 1, or it may comprise additional amino acids flanking such disclosed sequence, or may comprise of only a portion of the disclosed sequence immediately flanking the phosphorylatable amino acid (indicated in Column G by lowercase "y"). Polyclonal antibodies produced as described herein may be screened as further described below.

Monoclonal antibodies of the invention may be produced in a hybridoma cell line according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)).

The preferred epitope of a phosphorylation-site specific antibody of the invention is a peptide fragment consisting essentially of about 8 to 17 amino acids including the phosphorylatable tyrosine, wherein about 3 to 8 amino acids are positioned on each side of the phosphorylatable tyrosine (for example, the RasGAP3 tyrosine 765 phosphorylation site sequence disclosed in Row 71, Column G of Table 1), and antibodies of the invention thus specifically bind a target c-Src polypeptide comprising such epitopic sequence. Particularly preferred epitopes bound by the antibodies of the invention comprise all or part of a phosphorylatable site sequence listed in Column G of Table 1, including the phosphorylatable amino acid.

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies provided by the invention may be any type of immunoglobulins, including IgG, IgM, IgA, IgD, and IgE, including $F_{ab}$ or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The invention also provides immortalized cell lines that produce an antibody of the invention. For example, hybridoma clones, constructed as described above, that produce monoclonal antibodies to the c-Src-related signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czemik et al., *Methods in Enzymology,* 201: 264-283 (1991). For example, the antibodies may be screened against the phospho and non-phospho peptide library by ELISA to ensure specificity for both the desired antigen (i.e. that epitope including a phosphorylation site sequence enumerated in Column G of Table 1) and for reactivity only with the phosphorylated (or non-phosphorylated) form of the antigen. Peptide competition assays may be carried out to confirm lack of reactivity with other phospho-epitopes on the given c-Src-related signaling protein. The antibodies may also be tested by Western blotting against cell preparations containing the signaling protein, e.g. cell lines over-expressing the target protein, to confirm reactivity with the desired phosphorylated epitope/target.

Specificity against the desired phosphorylated epitope may also be examined by constructing mutants lacking phosphorylatable residues at positions outside the desired epitope known to be phosphorylated, or by mutating the desired phospho-epitope and confirming lack of reactivity. Phosphorylation-site specific antibodies of the invention may exhibit some limited cross-reactivity related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the c-Src-related signaling protein epitope for which the antibody of the invention is specific. In certain cases, polyclonal antisera may be exhibit some undesirable general cross-reactivity to phosphotyrosine, which may be removed by further purification of antisera, e.g. over a phosphotyramine column. Antibodies of the invention specifically bind their target protein (i.e. a protein listed in Column A of Table 1) only when phosphorylated (or only when not phosphorylated, as the case may be) at the site disclosed in corresponding Columns F/H, and do not (substantially) bind to the other form (as compared to the form for which the antibody is specific).

Antibodies may be further characterized via immunohistochemical (IHC) staining using normal and diseased tissues to examine c-Src-related phosphorylation and activation status in diseased tissue. IHC may be carried out according to well known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46:72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30 minutes on ice. Cells may then be stained with the primary phosphorylation-site specific antibody of the invention (which detects an c-Src-related signal transduction protein enumerated in Table 1), washed and labeled with a fluorescent-labeled secondary antibody. Additional fluorochrome-conjugated marker antibodies (e.g. CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Phosphorylation-site specific antibodies of the invention specifically bind to a human c-Src-related signal transduction protein or polypeptide only when phosphorylated at a disclosed site, but are not limited only to binding the human species, per se. The invention includes antibodies that also bind conserved and highly-homologous or identical phosphorylation sites in respective c-Src-related proteins from other species (e.g. mouse, rat, monkey, yeast), in addition to binding the human phosphorylation site. Highly-homologous sites conserved in other species can readily be identified by standard sequence comparisons, such as using BLAST, with the human c-Src-signal transduction protein phosphorylation sites disclosed herein.

C. Heavy-isotope Labeled Peptides (AQUA Peptides).

The novel c-Src-signaling protein phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within in a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2$H, $^{13}$C, $^{15}$N, $^{17}$O, $^{18}$O, or $^{34}$S, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS_n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for any of the 102 novel c-Src-related signaling protein phosphorylation sites disclosed herein (see Table 1/FIG. 2). Peptide standards for a given phosphorylation site (e.g. the tyrosine 251 site in CrkL—see Row 15 of Table 1) may be produced for both the phosphorylated and non-phosphorylated forms of the site (e.g. see CrkL site sequence in Column G, Row 15 of Table 1) and such standards employed in the AQUA methodology to detect and quantify both forms of such phosphorylation site in a biological sample.

The phosphorylation site peptide sequences disclosed herein (see Column G of Table 1/FIG. 2) are particularly well suited for development of corresponding AQUA peptides, since the IAP method by which they were identified (see Part A above and Example 1) inherently confirmed that such peptides are in fact produced by enzymatic digestion (trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) for the detection and/or quantification of any of the c-Src-related phosphorylation sites disclosed in Table 1 (see Column G) and/or their corresponding parent proteins/polypeptides (see Column A). Each such phosphorylation sequence may be considered a preferred AQUA peptide of the invention. Optimally, an AQUA peptide of the invention consists of a phosphorylation site sequence enumerated in Table 1. For example, an AQUA peptide comprising the sequence QKRVPCAyDKTALAL (SEQ ID NO: 14) (where y may be either phosphotyrosine or tyrosine, and where L=labeled leucine (e.g. $^{14}$C)) is provided for the quantification of phosphorylated (or non-phosphorylated) CrkL (Tyr251) in a biological sample (see Row 15 of Table 1, tyrosine 251 being the phosphorylatable residue within the site). However, it will be appreciated that a larger AQUA peptide comprising the disclosed phosphorylation site sequence (and additional residues downstream or upstream of it) may also be constructed. Similarly, a smaller AQUA peptide comprising less than all of the residues of a disclosed phosphorylation site sequence (but still comprising the phosphorylatable residue enumerated in Column F of Table 1/FIG. 2) may alternatively be constructed. Such larger or shorter AQUA peptides are within the scope of the present invention, and the selection and production of preferred AQUA peptides may be carried out as described above (see Gygi et al., Gerber et al. supra.).

Certain particularly preferred subsets of AQUA peptides provided by the invention are described above (corresponding to particular protein types/groups in Table 1, for example, Adaptor/Scaffold proteins or RNA Binding Proteins). Example 4 is provided to further illustrate the construction and use, by standard methods described above, of exemplary AQUA peptides provided by the invention. For example, AQUA peptides corresponding to the both the phosphorylated and non-phosphorylated forms of the disclosed MYPT1 tyrosine 764 phosphorylation site (SRTYDETyTRYRPVS (SEQ ID NO: 80)—see Row 81 of Table 1/FIG. 2) may be used to quantify the amount of phosphorylated MYPT1 (Tyr764) in biological sample, e.g. a tumor cell sample (or a sample before or after treatment with a test drug).

AQUA peptides of the invention may also be employed within a kit that comprises one or multiple AQUA peptide(s) provided herein (for the quantification of an c-Src-related signal transduction protein disclosed in Table 1), and, optionally, a second detecting reagent conjugated to a detectable group. For example, a kit may include AQUA peptides for both the phosphorylation and non-phosphorylated form of a phosphorylation site disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be highly useful in the further study of signal transduction anomalies underlying cancer, including c-Src-mediated cancers, and in identifying diagnostic/bio-markers of these diseases, new potential drug targets, and/or in monitoring the effects of test compounds on c-Src-related signal transduction proteins and pathways.

D. Immunoassay Formats

Antibodies provided by the invention may be advantageously employed in a variety of standard immunological assays (the use of AQUA peptides provided by the invention is described separately above). Assays may be homogeneous assays or heterogeneous assays. In a homogeneous assay the immunological reaction usually involves a phosphorylation-site specific antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phosphorylation-site specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof that may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et. al, "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of a target c-Src-related signal transduction protein is detectable compared to background.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation. Antibodies, or other target protein or target site-binding reagents, may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Antibodies of the invention may also be optimized for use in a flow cytometry assay to determine the activation/phosphorylation status of a target c-Src-related signal transduction protein in patients before, during, and after treatment with a drug targeted at inhibiting phosphorylation at such a protein at the phosphorylation site disclosed herein. For example, bone marrow cells or peripheral blood cells from patients may be analyzed by flow cytometry for target c-Src-related signal transduction protein phosphorylation, as well as for markers identifying various hematopoietic cell types. In this manner, activation status of the malignant cells may be specifically characterized. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 1% para-formaldehyde for 10 minutes at 37° C. followed by permeabilization in 90% methanol for 30 minutes on ice. Cells may then be stained with the primary antibody (a phospho-specific antibody of the invention), washed and labeled with a fluorescent-labeled secondary antibody. Alternatively, the cells may be stained with a fluorescent-labeled primary antibody. The cells would then be analyzed on a flow cytometer (e.g. a Beckman Coulter EPICS-XL) according to the specific protocols of the instrument used. Such an analysis would identify the presence of activated c-Src-related signal transduction protein(s) elated in the malignant cells and reveal the drug response on the targeted protein.

Alternatively, antibodies of the invention may be employed in immunohistochemical (IHC) staining to detect differences in signal transduction or protein activity using normal and diseased tissues. IHC may be carried out according to well-known techniques. See, e.g., ANTIBODIES: A LABORATORY MANUAL, supra. Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the invention provides a method for the multiplex detection of c-Src-related protein phosphorylation in a biological sample, the method comprising utilizing at two or more antibodies or AQUA peptides of the invention to detect the presence of two or more phosphorylated c-Src-related signaling proteins enumerated in Column A of Table 1/FIG. 2. In one preferred embodiment, two to five antibodies or AQUA peptides of the invention are employed in the method. In another preferred embodiment, six to ten antibodies or AQUA peptides of the invention are employed, while in another preferred embodiment eleven to twenty such reagents are employed.

Antibodies and/or AQUA peptides of the invention may also be employed within a kit that comprises at least one phosphorylation site-specific antibody or AQUA peptide of the invention (which binds to or detects an c-Src-related signal transduction protein disclosed in Table 1), and, optionally, a second antibody conjugated to a detectable group. In some embodies, the kit is suitable for multiplex assays and comprises two or more antibodies or AQUA peptides of the invention, and in some embodiments, comprises two to five, six to ten, or eleven to twenty reagents of the invention. The kit may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

Example 1

Isolation of Phosphotyrosine-Containing Peptides from Extracts of Activated NIH/3T3 Cells and Identification of Novel Phosphorylation Sites In order to discover previously unknown c-Src-related signal transduction protein phosphorylation sites, IAP isolation techniques were employed to identify phosphotyrosine-containing peptides in cell extracts from NIH/3T3 cells expressing an activated mutant form of c-Src kinase (Y527F). Increased c-Src activity has been demonstrated in a variety of human cancers, including breast, colon, pancreatic, ovarian, lung, esophogeal, and neural. See, e.g., Yeatman, supra. Thus, the c-Src activated 3T3 cell line was chosen to mimic signaling pathway activity in cancers involving activated c-Src.

Tryptic phosphotyrosine peptides were purified and analyzed from extracts of the 3T3 cell line as follows. Cells were cultured in DMEM medium supplemented with 10% bovine serum and penicillin/streptomycin under selection (1.5 µg/ml puromycin). Cells at about 80% confluency were starved in medium without serum for 3 hours. After complete aspiration of medium from the plates, cells were scraped off the plate in 10 ml lysis buffer per 2×10$^8$ cells (supplemented with 2.5 mM sodium pyrophosphate, 1 mM β-glycerol-phosphate) and sonicated.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and immobilized TLCK-trypsin (Pierce) was added at 1-2.5 ml beads (200 TAME units trypsin/ml) per 10$^9$ cells. Digestion was performed for 1-2 days at room temperature.

Trifluoroacetic acid (TFA) was added to protein digests to a final concentration of 1%, precipitate was removed by centrifugation, and digests were loaded onto Sep-Pak C$_{18}$ columns (Waters) equilibrated with 0.1% TFA. A column volume of 0.7-1.0 ml was used per 2×10⁸ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to 2×10⁸ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G agarose (Roche). Immobilized antibody (15 μl, 60 μg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 μl of 0.1% TFA at room temperature for 10 min.

Analysis by MALDI-TOF Mass Spectrometry.

A thin layer of α-cyano-4-hydroxy-cinnamic acid (ACHA) matrix was applied to a Bruker 384-spot MALDI target by spreading 5 μl of a saturated solution in MeCN/water (2/1, v/v) over an entire row of spots on the target; drying occurred in 2-5 sec. The IAP eluate (10 μl) was loaded onto an 0.2 μl C-18 ZipTip (Millipore), which then was washed with 5% formic acid. Peptide was eluted with 1 μl of 10 mg/ml ACHA in 60% methanol, 5% formic acid onto the MALDI target containing the thin layer of matrix. Samples were analyzed on a Bruker BiFlex III MALDI-TOF instrument in positive ion mode.

Analysis by LC-MS/MS Mass Spectrometry.

40 μl of IAP eluate were purified by 0.2 μl Stage tips. Peptides were eluted from the microcolumns with 1 μl of 40% MeCN, 0.1% TFA (fractions I and II) or 1 μl of 60% MeCN, 0.1% TFA (fraction III) into 7.6 μl of 0.4% acetic acid/ 0.005% heptafluorobutyric acid. This sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LCQ Deca XP Plus ion trap mass spectrometer essentially as described by Gygi et al., supra.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20; minimum TIC, 4×10⁵; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (for all other studies) (released on Apr. 29, 2003 and containing 37,490 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned.

In proteomics, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al. Mol Cell Proteomics 3: 531-533 (2004), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain an series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of 102 assigned sequences enumerated in Table 1/FIG. 2 herein were reviewed by at least three people to establish their credibility.

Example 2

Production of Phospho-Specific Polyclonal Antibodies for the Detection of c-Src-Related Signaling Protein Phosphorylation Polyclonal antibodies that specifically bind a c-Src-related signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, as further described below. Production of exemplary polyclonal antibodies is provided below.

A. Shb (Tyrosine 113).

A 15 amino acid phospho-peptide antigen, RAMCRLDy*CGGGGGG (SEQ ID NO: 28) (where y*=phosphotyrosine), that corresponds to the tyrosine 113 phosphorylation site in human Shb protein (see Row 29 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific Shb(tyr1134) polyclonal antibodies as described in Immunization/Screening below.

B. Rab7 (Tyrosine 183).

A 15 amino acid phospho-peptide antigen, QETEVELy*NEFPEPI (SEQ ID NO: 64) (where y*=phosphotyrosine), that corresponds to the tyrosine 183 phosphorylation site in human Rab7 protein (see Row 65 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific Rab7(tyr183) polyclonal antibodies as described in Immunization/Screening below.

C. Cortactin (Tyrosine 215).

A 15 amino acid phospho-peptide antigen, KSAVGFEy*QGKTEKH (SEQ ID NO: 58) (where y*=phosphotyrosine) that corresponds to the tyrosine 215 phosphorylation site in human Cortactin protein (see Row 59 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific Cortactin (tyr215) antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 µg antigen per rabbit). The rabbits are boosted with same antigen in incomplete Freund adjuvant (250 µg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto a non-phosphorylated synthetic peptide antigen-resin Knotes column to pull out antibodies that bind the non-phosphorylated form of the phosphorylation site. The flow through fraction is collected and applied onto a phospho-synthetic peptide antigen-resin column to isolate antibodies that bind the phosphorylated form of the site. After washing the column extensively, the bound antibodies (i.e. antibodies that bind a phosphorylated peptide described in A-C above, but do not bind the non-phosphorylated form of the peptide, are eluted and kept in antibody storage buffer.

The isolated antibody is then tested for phospho-specificity using Western blot assay using an appropriate cell line the expresses (or overexpresses) target phospho-protein (i.e. phosphorylated Shb, Rab7, or Cortactin, for example, NIH/ 3T3 cells. Cells are cultured in DMEM supplemented with 10% FCS and 5 U/ml IL-3. Before stimulation, the cells are starved in serum-free DMEM medium for 4 hours. The cells are then stimulated ligand (e.g. 50 ng/ml) for 5 minutes. Cell are collected, washed with PBS and directly lysed in cell lysis buffer. The protein concentration of cell lysates are then measured. The loading buffer is added into cell lysate and the mixture is boiled at 100° C. for 5 minutes. 20 µl (10 µg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phospho-specific antibody is used at dilution 1:1000. Phosphorylation-site specificity of the antibody will be shown by binding of only the phosphorylated form of the target protein. Isolated phospho-specific polyclonal antibody does not recognize the target protein when not phosphorylated at the appropriate phosphorylation site in the non-stimulated cells (e.g. Shb is not bound when not phosphorylated at tyrosine 113).

In order to confirm the specificity of the isolated antibody, different cell lysates containing various phosphorylated signal transduction proteins other than the target protein are prepared. The Western blot assay is preformed again using these cell lysates. The phospho-specific polyclonal antibody isolated as described above is used (1:1000 dilution) to test reactivity with the different phosphorylated non-target proteins on Western blot membrane. The phospho-specific antibody does not significantly cross-react with other phosphorylated signal transduction proteins, although occasionally slight binding with a highly-homologous phosphorylation-site on another protein may be observed. In such case the antibody may be further purified using affinity chromatography, or the specific immunoreactivity cloned by rabbit hybridoma technology.

Example 3

Production of Phospho-Specific Monoclonal Antibodies for the Detection of c-Src-Related Signaling Protein Phosphorylation Monoclonal antibodies that specifically bind a c-Src-related signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, and harvesting spleen cells from such animals to produce fusion hybridomas, as further described below. Production of exemplary monoclonal antibodies is provided below.

A. eIF4H (Tyrosine 45).

A 15 amino acid phospho-peptide antigen, TEPPYTAy*VGNLPFN (SEQ ID NO: 94) (where y*=phosphotyrosine) that corresponds to the tyrosine 45 phosphorylation site in human eIF4H protein (see Row 95 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal eIF4H(tyr45) antibodies as described in Immunization/Fusion/Screening below.

B. PTP-delta (Tyrosine 677).

A 15 amino acid phospho-peptide antigen, QLEKWTEy*RITVTAH (SEQ ID NO: 84) (where y*=phosphotyrosine) that corresponds to the tyrosine 677 phosphorylation site in human PTP-delta phosphatase (see Row 85 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal PTP-delta (tyr677) antibodies as described in Immunization/Fusion/Screening below.

C. Dynamin-1 (Tyrosine 354).

A 15 amino acid phospho-peptide antigen, SGDQIDTy*ELSGGAR (SEQ ID NO: 102) (where y*=phosphotyrosine) that corresponds to the tyrosine 354 phosphorylation site in human Dynamin-1 protein (see Row 103 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal Dynamin-1 (tyr354) antibodies as described in Immunization/Fusion/Screening below.

Immunization/Fusion/Screening.

A synthetic phospho-peptide antigen as described in A-C above is coupled to KLH, and BALB/C mice are injected intradermally (ID) on the back with antigen in complete Freunds adjuvant (e.g. 50 μg antigen per mouse). The mice are boosted with same antigen in incomplete Freund adjuvant (e.g. 25 μg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the eIF4H, PTP-delta, or Dynamin-1 phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target (e.g. eIF4H phosphorylated at tyrosine 45).

Example 4

Production and Use of AQUA Peptides for the Quantification of c-Src-Related Signaling Protein Phosphorylation Heavy-isotope labeled peptides (AQUA peptides (internal standards)) for the detection and quantification of an c-Src-related signal transduction protein only when phosphorylated at the respective phosphorylation site disclosed herein (see Table 1) are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the $MS^n$ and LC-SRM signature of the peptide standard is validated, and the AQUA peptide is used to quantify native peptide in a biological sample, such as a digested cell extract. Production and use of exemplary AQUA peptides is provided below.

A. DAB2 (Tyrosine 342).

An AQUA peptide having a sequence corresponding to the tyrosine 342 phosphorylation site in human DAB2 protein, PLNVDTDy*FGQQFDQ (y*=phosphotyrosine) (see Row 16 in Table 1 (SEQ ID NO: 15)) but incorporating $^{14}C/^{15}N$-labeled leucine (indicated by bold L) is constructed according to standard synthesis techniques using, e.g., a Rainin/Protein Technologies, Inc., Symphony peptide synthesizer (see Merrifield, supra.) as further described below in Synthesis & MS/MS Signature. The DAB2 (tyr342) AQUA peptide is then spiked into a biological sample to quantify the amount of phosphorylated DAB2(tyr342) in the sample, as further described below in Analysis & Quantification.

B. NEDD5 (Tyrosine 17).

An AQUA peptide having a sequence corresponding to the tyrosine 17 phosphorylation site in human NEDD5 protein, INPETPGy*VGFANLP (y*=phosphotyrosine) (see Row 42 in Table 1 (SEQ ID NO: 41)) but incorporating $^{14}C/^{15}N$-labeled proline (indicated by bold P) is constructed according to standard synthesis techniques using, e.g., a Rainin/Protein Technologies, Inc., Symphony peptide synthesizer (see Merrifield, supra.) as further described below in Synthesis & MS/MS Signature. The NEDD5(tyr17) AQUA peptide is then spiked into a biological sample to quantify the amount of phosphorylated NEDD5(tyr17) in the sample, as further described below in Analysis & Quantification.

C. PL10 (Tyrosine 67).

An AQUA peptide having a sequence corresponding to the tyrosine 67 phosphorylation site in human PL10 Helicase, WSKDKDAy*SSFGSRS (y*=phosphotyrosine) (see Row 76 in Table 1 (SEQ ID NO: 75)) but incorporating $^{14}C/^{15}N$-labeled phenylalanine (indicated by bold F) is constructed according to standard synthesis techniques using, e.g., a Rainin/Protein Technologies, Inc., Symphony peptide synthesizer (see Merrifield, supra.) as further described below in Synthesis & MS/MS Signature. The PL10(tyr67) AQUA peptide is then spiked into a biological sample to quantify the amount of phosphorylated PL10 (tyr67) in the sample, as further described below in Analysis & Quantification.

D. P130Cas (Tyrosine 228).

An AQUA peptide having a sequence corresponding to the tyrosine 228 phosphorylation site in human P130Cas protein, RVGQGYVy*EAQTEQ (y*=phosphotyrosine) (see Row 109 in Table 1 (SEQ ID NO: 108)) but incorporating $^{14}$C/$^{15}$N-labeled valine (indicated by bold V) is constructed according to standard synthesis techniques using, e.g., a Rainin/Protein Technologies, Inc., Symphony peptide synthesizer (see Merrifield, supra.) as further described below in Synthesis & MS/MS Signature. The P130C as(tyr228) AQUA peptide is then spiked into a biological sample to quantify the amount of phosphorylated P130Cas(tyr228) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}$N and five to nine $^{13}$C atoms may be obtained from Cambridge Isotope Laboratories (Andover, Mass.). Preloaded Wang resins may be obtained from Applied Biosystems. Synthesis scales may vary from 5 to 25 μmol. Amino acids are activated in situ with 1-H-benzotriazolium, 1-bis (dimethylamino) methylene]-hexafluorophosphate(1-),3-oxide: 1-hydroxybenzotriazole hydrate and coupled at a 5-fold molar excess over peptide. Each coupling cycle is followed by capping with acetic anhydride to avoid accumulation of one-residue deletion peptide byproducts. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g. a phosphorylated protein of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole). On the DecaXP, parent ions are isolated at 1.6 m/z width, the ion injection time being limited to 150 ms per microscan, with two microscans per peptide averaged, and with an AGC setting of 1×10$^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds a human c-Src-related signaling protein, wherein said signaling protein is PI3K p85-beta, only when said signaling protein is phosphorylated at the tyrosine at position 458, comprised within the phosphorylatable peptide sequence listed in SEQ ID NO: 77, wherein said antibody does not bind said signaling protein when not phosphorylated at said tyrosine.

2. An immortalized cell line producing the antibody of claim 1.

3. The cell line of claim 2, wherein said immortalized cell line is a rabbit hybridoma or a mouse hybridoma.

* * * * *

SEQUENCE LISTING

```
<160> NUMBER OF SEQ ID NOS: 102

<210> SEQ ID NO 1
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 1

Ser Glu Asp Arg Asp Leu Leu Tyr Ser Ile Asp Ala Tyr Arg Ser
1               5                   10                  15

<210> SEQ ID NO 2
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

-continued

<400> SEQUENCE: 2

Pro Asp Gly Tyr Gly Arg His Tyr Glu Asp Gly Tyr Pro Gly Gly
1               5                   10                  15

<210> SEQ ID NO 3
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 3

Gly Arg His Tyr Glu Asp Gly Tyr Pro Gly Gly Ser Asp Asn Tyr
1               5                   10                  15

<210> SEQ ID NO 4
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 4

Ala Pro Ser Arg Gln Asp Val Tyr Gly Pro Gln Pro Gln Val Arg
1               5                   10                  15

<210> SEQ ID NO 5
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 5

His Arg Phe His Pro Glu Pro Tyr Gly Leu Glu Asp Asp Gln Arg
1               5                   10                  15

<210> SEQ ID NO 6
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 6

Glu Glu Val Pro Pro Asp Gln Tyr Tyr Trp Ala Pro Leu Ala Gln
1               5                   10                  15

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated -continued

<400> SEQUENCE: 7

Gln Asp His Asn His Leu Leu Tyr Ser Thr Ile Pro Arg Met Gln
1               5                   10                  15

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 8

Arg Ser Ser Thr Glu Thr Cys Tyr Ser Ala Ile Pro Lys Ser Ser
1               5                   10                  15

<210> SEQ ID NO 9
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 9

Gln Ser Lys Leu Ser Asp Ser Tyr Ser Asn Thr Leu Pro Val Arg
1               5                   10                  15

<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 10

Gly Thr Phe Lys Gln Arg Pro Tyr Ser Val Ala Val Pro Ala Phe
1               5                   10                  15

<210> SEQ ID NO 11
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 11

Phe Ser Gln Gly Leu Asp Asp Tyr Gly Ala Arg Ser Val Ser Arg
1               5                   10                  15

<210> SEQ ID NO 12
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated -continued

```
<400> SEQUENCE: 12

Gly Pro Leu Asp Gly Ser Pro Tyr Ala Gln Val Gln Arg Val Pro
1               5                   10                  15

<210> SEQ ID NO 13
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 13

Ala Ser Gln Asp Tyr Asp Gln Leu Pro Ser Ser Ser Asp
1               5                   10

<210> SEQ ID NO 14
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 14

Gln Lys Arg Val Pro Cys Ala Tyr Asp Lys Thr Ala Leu Ala Leu
1               5                   10                  15

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 15

Pro Leu Asn Val Asp Thr Asp Tyr Phe Gly Gln Gln Phe Asp Gln
1               5                   10                  15

<210> SEQ ID NO 16
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 16

Val His Ser Lys Lys Pro Leu Tyr Trp Asp Leu Tyr Gly His Val
1               5                   10                  15

<210> SEQ ID NO 17
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

-continued

<400> SEQUENCE: 17

Lys Pro Leu Tyr Trp Asp Leu Tyr Gly His Val Gln Gln Gln Leu
1               5                   10                  15

<210> SEQ ID NO 18
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 18

Glu Glu Gly Tyr Glu Leu Pro Tyr Asn Pro Ala Thr Asp Asp Tyr
1               5                   10                  15

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 19

Asp Tyr Pro Pro Ala Asp Gly Tyr Ala Tyr Ser Ser Ser Met Tyr
1               5                   10                  15

<210> SEQ ID NO 20
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 20

Pro Pro Ala Asp Gly Tyr Ala Tyr Ser Ser Ser Met Tyr His Arg
1               5                   10                  15

<210> SEQ ID NO 21
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 21

Val Glu Arg Asn Thr Glu Phe Tyr His Ile Pro Thr His Ser Asp
1               5                   10                  15

<210> SEQ ID NO 22
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated -continued

<400> SEQUENCE: 22

Arg Val Gly Gln Gly Tyr Val Tyr Glu Ala Ala Gln Thr Glu Gln
1               5                   10                  15

<210> SEQ ID NO 23
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 23

Ser Pro Ala Ala Glu Asp Val Tyr Asp Val Pro Pro Pro Ala Pro
1               5                   10                  15

<210> SEQ ID NO 24
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 24

Pro Pro Pro Ala Pro Asp Leu Tyr Asp Val Pro Pro Gly Leu Arg
1               5                   10                  15

<210> SEQ ID NO 25
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 25

Cys Ala Pro Asp Lys Arg Ile Tyr Gln Phe Thr Ala Ala Ser Pro
1               5                   10                  15

<210> SEQ ID NO 26
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 26

Gln Pro Ile Asp Asp Glu Ile Tyr Glu Glu Leu Pro Glu Glu Glu
1               5                   10                  15

<210> SEQ ID NO 27
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

```
<400> SEQUENCE: 27

Asp Ala Glu Asp Gly Asp Glu Tyr Asp Asp Pro Phe Ala Gly Pro
1               5                   10                  15

<210> SEQ ID NO 28
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 28

Arg Ala Met Cys Arg Leu Asp Tyr Cys Gly Gly Gly Gly Gly Gly
1               5                   10                  15

<210> SEQ ID NO 29
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 29

Ser Leu Asp Arg His Ala Ala Tyr Gly Gly Tyr Ser Thr Pro Glu
1               5                   10                  15

<210> SEQ ID NO 30
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 30

Arg His Ala Ala Tyr Gly Gly Tyr Ser Thr Pro Glu Asp Arg Arg
1               5                   10                  15

<210> SEQ ID NO 31
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 31

Glu Glu Gln Pro Ala Pro Ala Tyr Glu Val His Asn Arg Tyr Arg
1               5                   10                  15

<210> SEQ ID NO 32
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

-continued

<400> SEQUENCE: 32

Tyr Arg Pro Glu Ala Gln Pro Tyr Ser Ser Thr Gly Pro Lys Ser
1               5                   10                  15

<210> SEQ ID NO 33
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 33

Val Arg Glu Asp Ala Val Leu Tyr Leu Leu Glu Ile Pro Lys Gly
1               5                   10                  15

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 34

Gly Pro Ser Ser Gly Gln Ile Tyr Gly Pro Gly Pro Arg Gly Tyr
1               5                   10                  15

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 35

Gln Gly Arg Tyr Tyr Glu Pro Tyr Tyr Ala Ala Gly Pro Ser Tyr
1               5                   10                  15

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 36

Ala His Arg Ser Leu Glu Gln Tyr Asp Gln Val Pro Asp Gly Val
1               5                   10                  15

<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated -continued

```
<400> SEQUENCE: 37

Lys Lys Ser Lys Gln Pro Leu Tyr Ser Ser Ile Val Thr Val Glu
1               5                   10                  15

<210> SEQ ID NO 38
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 38

Glu Gly Pro Ser Gly Ala Leu Tyr Ala Arg Val Ala Arg Arg Glu
1               5                   10                  15

<210> SEQ ID NO 39
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 39

His Ser Thr Pro Pro Ser Ala Tyr Gly Ser Val Lys Pro Tyr Thr
1               5                   10                  15

<210> SEQ ID NO 40
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 40

Arg Tyr Lys Ser Tyr Ser Pro Tyr Asp Met Leu Glu Ser Ile Lys
1               5                   10                  15

<210> SEQ ID NO 41
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 41

Ile Asn Pro Glu Thr Pro Gly Tyr Val Gly Phe Ala Asn Leu Pro
1               5                   10                  15

<210> SEQ ID NO 42
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 42

Arg Lys Leu Ala Ala Val Thr Tyr Asn Gly Val Asp Asn Asn Lys
1               5                   10                  15

<210> SEQ ID NO 43
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 43

Glu Arg Leu Gly Glu Asp Pro Tyr Tyr Thr Glu Asn Gly Gly Gly
1               5                   10                  15

<210> SEQ ID NO 44
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 44

Glu Asn Gly Gly Gly Gln Gly Tyr Ser Ser Gly Pro Gly Ala Ser
1               5                   10                  15

<210> SEQ ID NO 45
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 45

Gly Ile Asp Leu Gly Thr Thr Tyr Ser Cys Val Gly Val Phe Gln
1               5                   10                  15

<210> SEQ ID NO 46
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 46

Val Thr His Thr Val Pro Ile Tyr Glu Gly Tyr Ala Leu Pro His
1               5                   10                  15

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 47

Gly Met Gly Gln Lys Asp Ser Tyr Val Gly Asp Lys Ala Gln Ser
1               5                  10                  15

<210> SEQ ID NO 48
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 48

Met Thr Tyr Val Ser Ser Phe Tyr His Ala Phe Ser Gly Ala Gln
1               5                  10                  15

<210> SEQ ID NO 49
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 49

Ala Glu Val Gly Thr Gly Gln Tyr Ala Thr Thr Lys Gly Ile Ser
1               5                  10                  15

<210> SEQ ID NO 50
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 50

Trp Ser Leu Pro Asn Pro Glu Tyr Tyr Thr Leu Arg Tyr Ala Asp
1               5                  10                  15

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 51

Arg Val Asp Gly Asp Asn Ile Tyr Val Arg His Ser Asn Leu Met
1               5                  10                  15

<210> SEQ ID NO 52
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

<400> SEQUENCE: 52

Thr Glu Thr Lys Thr Ile Thr Tyr Glu Ser Pro Gln Ile Asp Gly
1               5                   10                  15

<210> SEQ ID NO 53
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 53

Gln Ile Lys Arg Asn Arg Tyr Tyr Asp Glu Asp Glu Asp Glu Glu
1               5                   10                  15

<210> SEQ ID NO 54
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 54

Ser Lys Gly Tyr Tyr Ser Pro Tyr Ser Val Ser Gly Ser Gly Ser
1               5                   10                  15

<210> SEQ ID NO 55
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 55

Ile Ala Gln Gly Asn Glu Asn Tyr Ala Gly Ile Ala Ala Arg Asp
1               5                   10                  15

<210> SEQ ID NO 56
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 56

Pro Ser Thr Ser Arg Ser Leu Tyr Ser Ser Ser Pro Gly Gly Ala
1               5                   10                  15

<210> SEQ ID NO 57
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

```
<400> SEQUENCE: 57

Ser Ser Ser Pro Gly Gly Ala Tyr Val Thr Arg Ser Ser Ala Val
1               5                   10                  15

<210> SEQ ID NO 58
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 58

Lys Ser Ala Val Gly Phe Glu Tyr Gln Gly Lys Thr Glu Lys His
1               5                   10                  15

<210> SEQ ID NO 59
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 59

Pro Thr Val Glu Val Asp Leu Tyr Thr Ala Lys Gly Leu Phe Arg
1               5                   10                  15

<210> SEQ ID NO 60
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 60

Gly Phe Gln Tyr Lys Gly Thr Tyr Lys Gly Thr His Lys His
1               5                   10

<210> SEQ ID NO 61
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 61

Ile Ser Trp Tyr Asp Asn Glu Tyr Gly Tyr Ser Asn Arg Val Val
1               5                   10                  15

<210> SEQ ID NO 62
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 62

Glu Asn Arg Phe Ser Gly Trp Tyr Asp Ala Asp Leu Ser Pro Ala
1               5                   10                  15

<210> SEQ ID NO 63
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 63

Ile Ser Trp Tyr Asn Asn Glu Tyr Gly Tyr Ser Asn Arg Glu Glu
1               5                   10                  15

<210> SEQ ID NO 64
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 64

Gln Glu Thr Glu Val Glu Leu Tyr Asn Glu Phe Pro Glu Pro Ile
1               5                   10                  15

<210> SEQ ID NO 65
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 65

Met Arg Glu Ser Glu Gly Leu Tyr Gly Gln Pro Gly Asp Glu Thr
1               5                   10                  15

<210> SEQ ID NO 66
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 66

Glu Leu Glu Asp Asp Ala Ile Tyr Ser Val His Val Pro Ala Gly
1               5                   10                  15

<210> SEQ ID NO 67
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 67

Val His Val Pro Ala Gly Leu Tyr Arg Ile Arg Lys Gly Val Ser
1               5                   10                  15

<210> SEQ ID NO 68
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 68

Leu Val Lys Leu Gln Gln Thr Tyr Ser Ala Leu Asn Ser Lys Ala
1               5                   10                  15

<210> SEQ ID NO 69
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 69

Ala Pro Gln Ile Gln Asp Leu Tyr Gly Lys Val Asp Phe Thr Glu
1               5                   10                  15

<210> SEQ ID NO 70
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 70

Asp Gly Pro Glu Gln Glu Glu Tyr Ser Thr Phe Val Ile Asp Asp
1               5                   10                  15

<210> SEQ ID NO 71
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 71

Lys Pro Ser Thr Asp Pro Leu Tyr Asp Thr Pro Asp Thr Arg Gly
1               5                   10                  15

<210> SEQ ID NO 72
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 72

Gly Ser His Arg Leu Ser Ile Tyr Glu Glu Trp Asp Pro Phe Arg
1               5                   10                  15

<210> SEQ ID NO 73
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 73

Asp Asp Arg Gly Arg Gly Asp Tyr Asp Gly Ile Gly Gly Arg Gly
1               5                   10                  15

<210> SEQ ID NO 74
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 74

Asp Asp His Gly Arg Asn Asp Tyr Asp Gly Ile Gly Gly Arg Asp
1               5                   10                  15

<210> SEQ ID NO 75
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 75

Trp Ser Lys Asp Lys Asp Ala Tyr Ser Ser Phe Gly Ser Arg Ser
1               5                   10                  15

<210> SEQ ID NO 76
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 76

Ser Glu Arg Glu Asn Val Gln Tyr Ser Ser Val Asn Gly Asp Cys
1               5                   10                  15

<210> SEQ ID NO 77
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 77

Ser Arg Glu Tyr Asp Gln Leu Tyr Glu Glu Tyr Thr Arg Thr Ser
1               5                   10                  15

<210> SEQ ID NO 78
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 78

Pro Tyr Glu Pro Val Ser Pro Tyr Ser Cys Arg Glu Ala Pro Cys
1               5                   10                  15

<210> SEQ ID NO 79
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 79

Phe Gln Asp Ser Ile Phe Glu Tyr Phe Asn Thr Ala Pro Leu Ala
1               5                   10                  15

<210> SEQ ID NO 80
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 80

Ser Arg Thr Tyr Asp Glu Thr Tyr Thr Arg Tyr Arg Pro Val Ser
1               5                   10                  15

<210> SEQ ID NO 81
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 81

Ala Gln Ala Pro Ala Ser Pro Tyr Asn Asp Tyr Glu Gly Arg Lys
1               5                   10                  15

<210> SEQ ID NO 82
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

<400> SEQUENCE: 82

Pro Ala Ser Pro Tyr Asn Asp Tyr Glu Gly Arg Lys Gly Asp Ser
1               5                   10                  15

<210> SEQ ID NO 83
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 83

Asn Ser Ser Asp Thr Thr Lys Tyr Leu Leu Glu Gln Leu Glu Lys
1               5                   10                  15

<210> SEQ ID NO 84
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 84

Gln Leu Glu Lys Trp Thr Glu Tyr Arg Ile Thr Val Thr Ala His
1               5                   10                  15

<210> SEQ ID NO 85
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 85

Lys Asn Asn Ala Ser Thr Asp Tyr Asp Leu Ser Asp Lys Ser Ile
1               5                   10                  15

<210> SEQ ID NO 86
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 86

Lys Asp Pro Asp Ser Asn Pro Tyr Ser Leu Leu Asp Asn Thr Glu
1               5                   10                  15

<210> SEQ ID NO 87
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

```
<400> SEQUENCE: 87

Lys Asp Pro Asp Ser Asn Pro Tyr Ser Leu Leu Asp Thr Ser Glu
1               5                   10                  15

<210> SEQ ID NO 88
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 88

Tyr Ser Gly Ser Gln Gly Gly Tyr Asp Arg Tyr Ser Gly Gly Asn
1               5                   10                  15

<210> SEQ ID NO 89
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 89

Gly Arg Glu Val Asp Ser Glu Tyr Glu Ala Arg Ser Arg Leu Gln
1               5                   10                  15

<210> SEQ ID NO 90
<211> LENGTH: 8
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 90

Ala Thr Gln Asp Ser Gly Phe Tyr
1               5

<210> SEQ ID NO 91
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 91

Phe Thr Pro Asp His Val Val Tyr Ala Arg Ser Lys Thr Ala Val
1               5                   10                  15

<210> SEQ ID NO 92
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

```
<400> SEQUENCE: 92

Thr Thr Thr Gly His Leu Ile Tyr Lys Cys Gly Gly Ile Asp Lys
1               5                   10                  15

<210> SEQ ID NO 93
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 93

Asp Thr Tyr Asp Asp Arg Ala Tyr Ser Ser Phe Gly Gly Gly Arg
1               5                   10                  15

<210> SEQ ID NO 94
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 94

Thr Glu Pro Pro Tyr Thr Ala Tyr Val Gly Asn Leu Pro Phe Asn
1               5                   10                  15

<210> SEQ ID NO 95
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 95

Ala Ile Pro Ser Ala Pro Leu Tyr Glu Glu Ile Thr Tyr Ser Gly
1               5                   10                  15

<210> SEQ ID NO 96
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 96

Pro Leu Tyr Glu Glu Ile Thr Tyr Ser Gly Ile Ser Asp Gly Leu
1               5                   10                  15

<210> SEQ ID NO 97
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
```

<400> SEQUENCE: 97

Phe Leu Arg Glu Asn Pro Tyr Tyr Asp Ser Arg Val Val Gly Lys
1               5                   10                  15

<210> SEQ ID NO 98
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 98

Glu Arg Ile Ser Glu Gln Thr Tyr Gln Leu Ser Arg Trp Thr Pro
1               5                   10                  15

<210> SEQ ID NO 99
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 99

Gln Pro Ser Cys Lys Ala Leu Tyr Asp Phe Glu Pro Glu Asn Asp
1               5                   10                  15

<210> SEQ ID NO 100
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 100

Ile Ala Ile Ile Val Gly Asp Tyr Gly Pro Met Trp Val Tyr Pro
1               5                   10                  15

<210> SEQ ID NO 101
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 101

Pro Thr Tyr Asp Glu Ile Phe Tyr Thr Leu Ser Pro Val Asn Gly
1               5                   10                  15

<210> SEQ ID NO 102
<211> LENGTH: 15
<212> TYPE: PRT
<213> ORGANISM: Homo sapiens

```
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 102

Ser Gly Asp Gln Ile Asp Thr Tyr Glu Leu Ser Gly Gly Ala Arg
1               5                   10                  15
```